(12) United States Patent
Nishide et al.

(10) Patent No.: US 6,845,144 B2
(45) Date of Patent: Jan. 18, 2005

(54) THREE DIMENSIONAL BACK PROJECTION METHOD AND AN X-RAY CT APPARATUS

(75) Inventors: Akihiko Nishide, Tokyo (JP); Sarah K. Patch, Milwaukee, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/360,588

(22) Filed: Feb. 8, 2003

(65) Prior Publication Data

US 2004/0156469 A1 Aug. 12, 2004

(51) Int. Cl.[7] ................................................. A61B 6/03
(52) U.S. Cl. ............................................ 378/15; 378/901
(58) Field of Search ............................. 378/4, 15, 901; 382/132

(56) References Cited

U.S. PATENT DOCUMENTS

| | | | |
|---|---|---|---|
| 5,056,146 A | | 10/1991 | Nishide |
| 5,309,356 A | | 5/1994 | Nishide et al. |
| 5,402,337 A | | 3/1995 | Nishide |
| 5,796,803 A | * | 8/1998 | Flohr et al. .................... 378/15 |
| 5,838,756 A | * | 11/1998 | Taguchi et al. ................. 378/4 |
| 6,466,639 B2 | | 10/2002 | Nukui et al. |
| 6,470,206 B2 | | 10/2002 | Nukui et al. |
| 6,665,369 B2 | * | 12/2003 | Ukita ............................ 378/4 |
| 2004/0013294 A1 | * | 1/2004 | De Man et al. ............ 382/132 |

* cited by examiner

*Primary Examiner*—Edward J. Glick
*Assistant Examiner*—Chih-Cheng Glen Kao
(74) *Attorney, Agent, or Firm*—Carl B. Horton, Esq.; Armstrong Teasdale LLP

(57) ABSTRACT

To perform cone beam reconstruction by using projection data correctly corresponding to X-ray beam having passed through each pixel in the reconstruction area, data D1 is obtained which is plane projected to a plane based on projection data D0. Then, plane projection data D1 to the projection plane pp is projected to the reconstruction area in the direction of X-ray transmission to obtain back projection pixel data D2. Thereafter, back projection pixel data D2 will be added for each corresponding pixel for all views to obtain back projection data D3. The present invention provides reconstruction by device of projection data correctly corresponding to the X-ray beam having passed through the reconstruction area. Through the plane projection to a plane the operation will become simplified and faster.

17 Claims, 18 Drawing Sheets

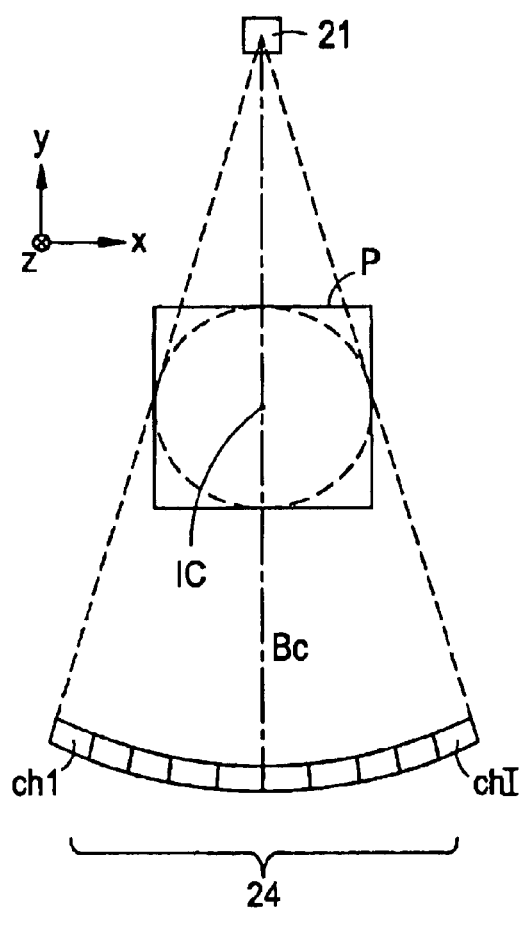
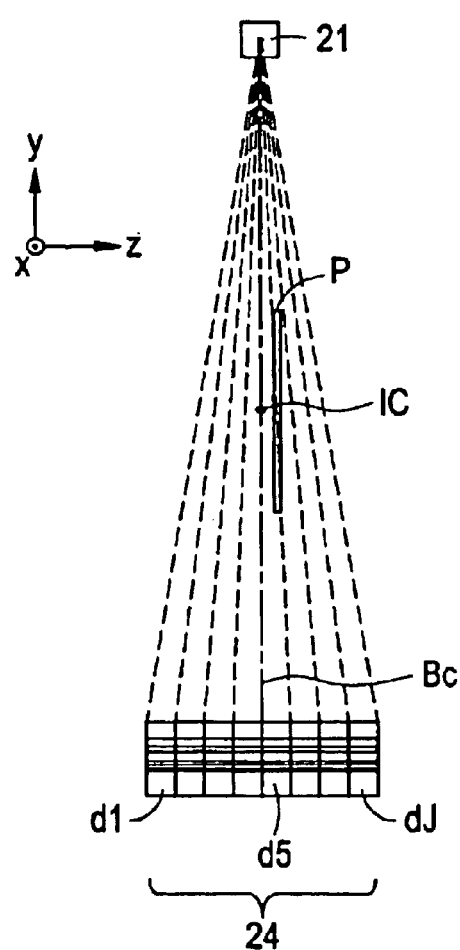
FIG. 1A
FIG. 1B

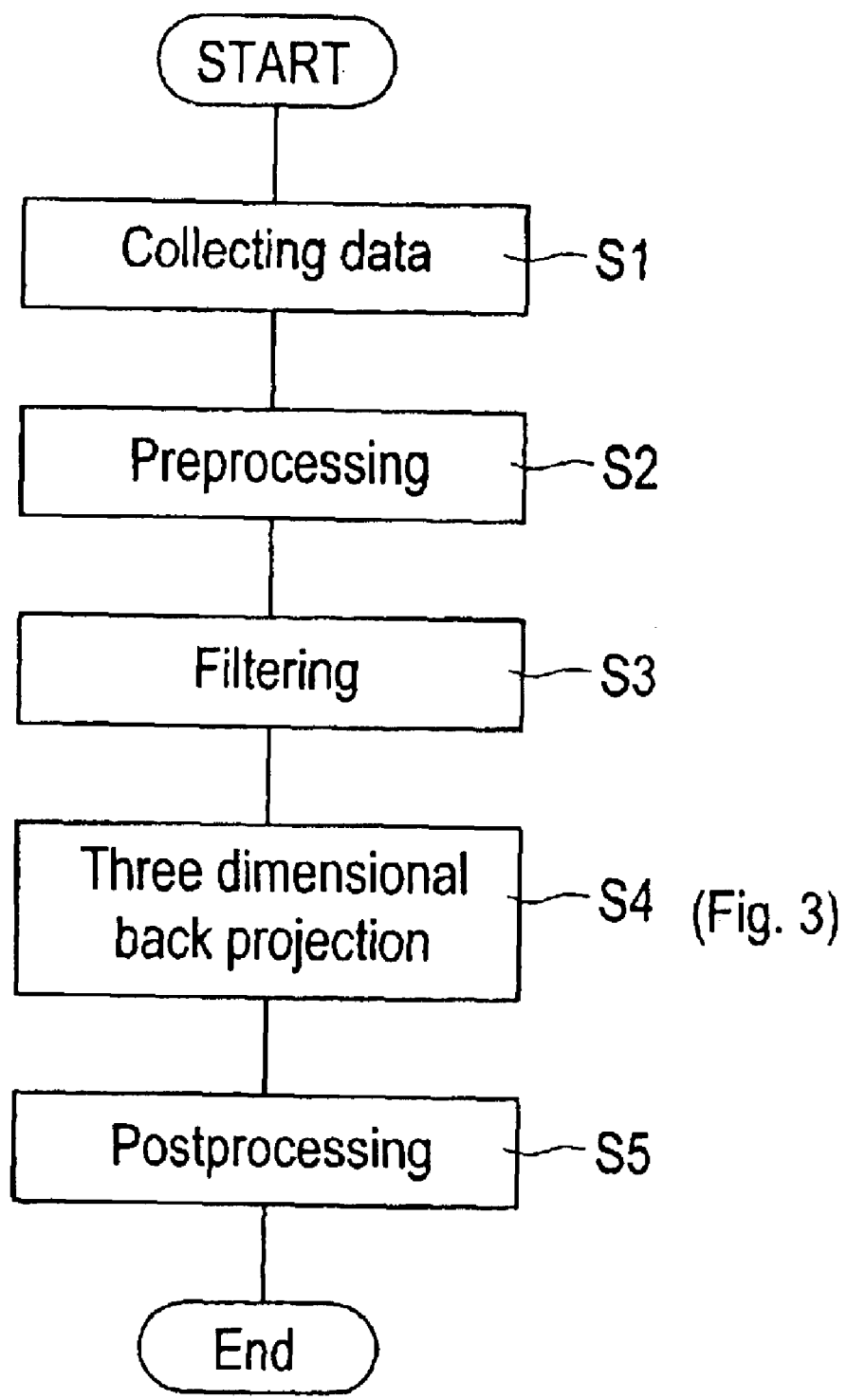

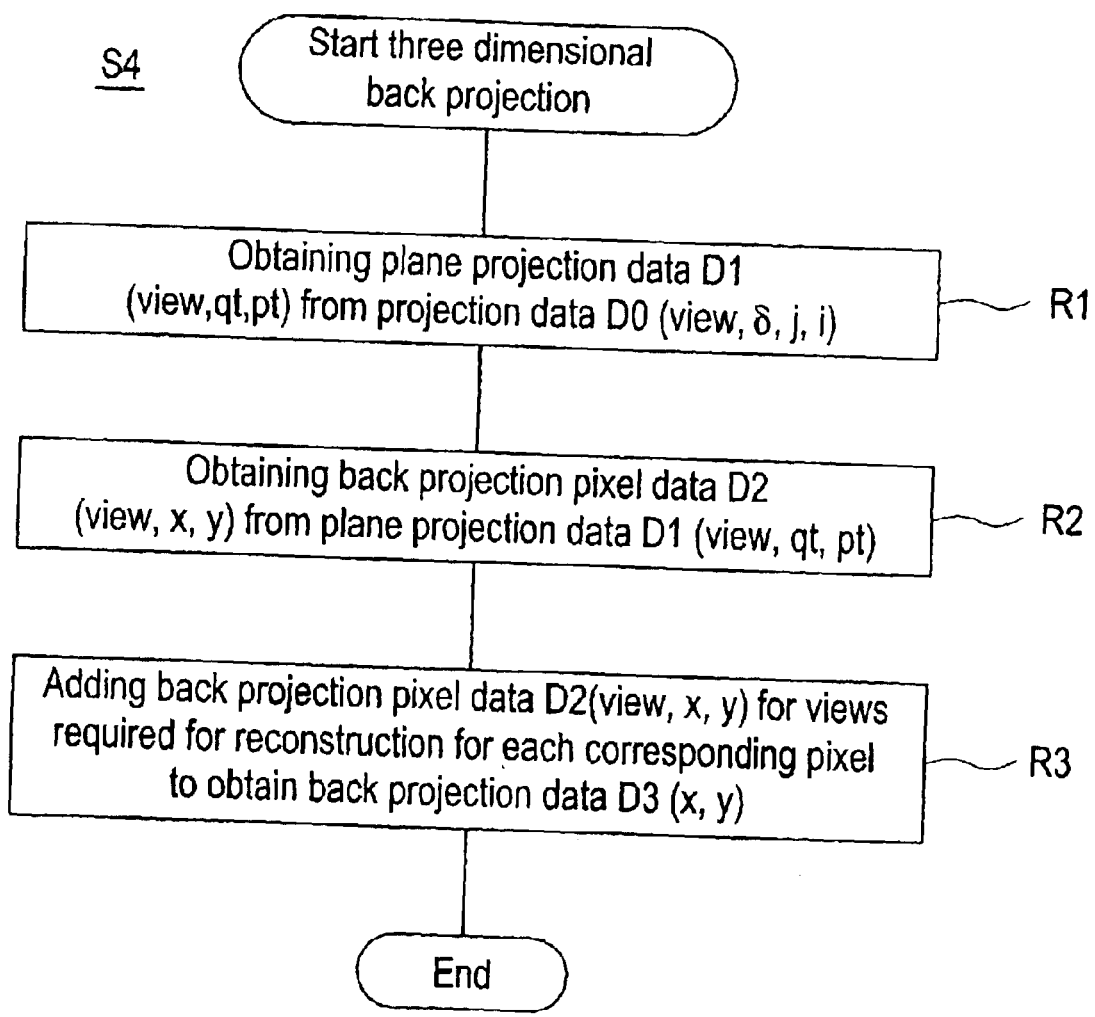

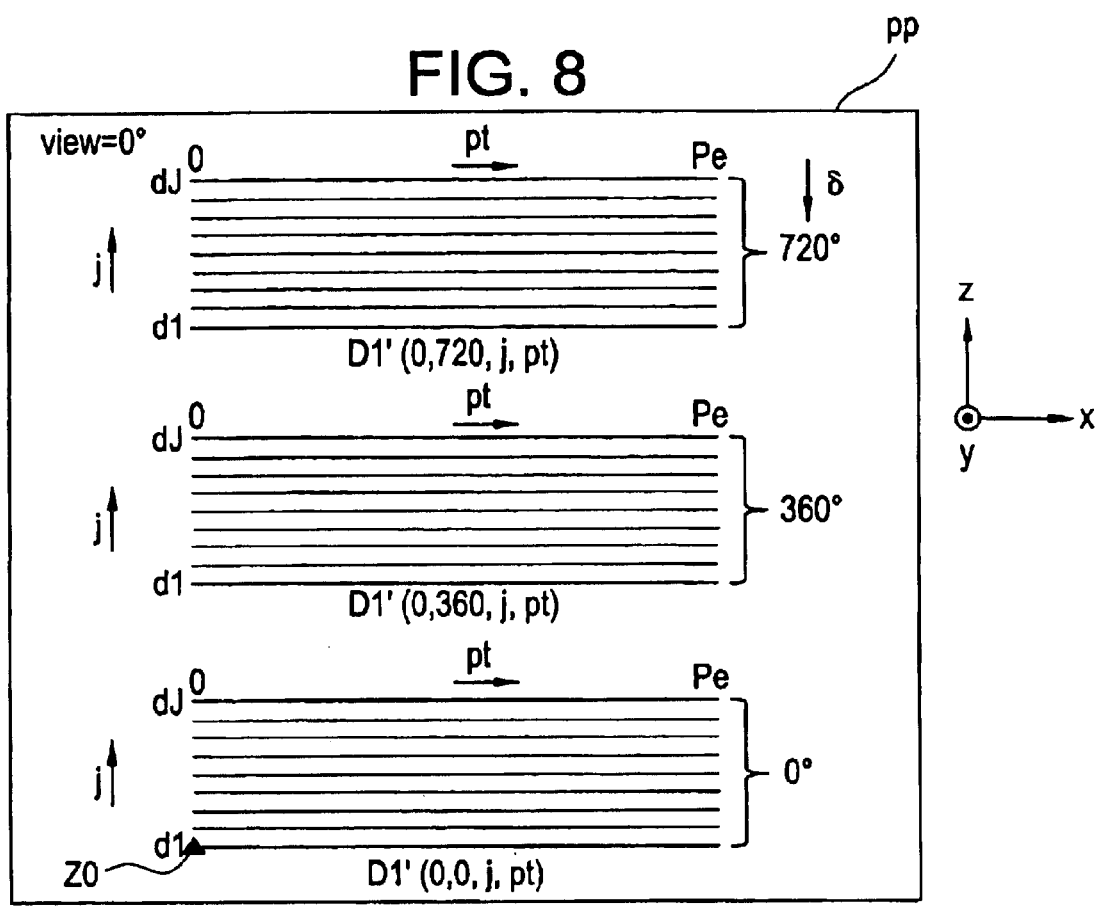
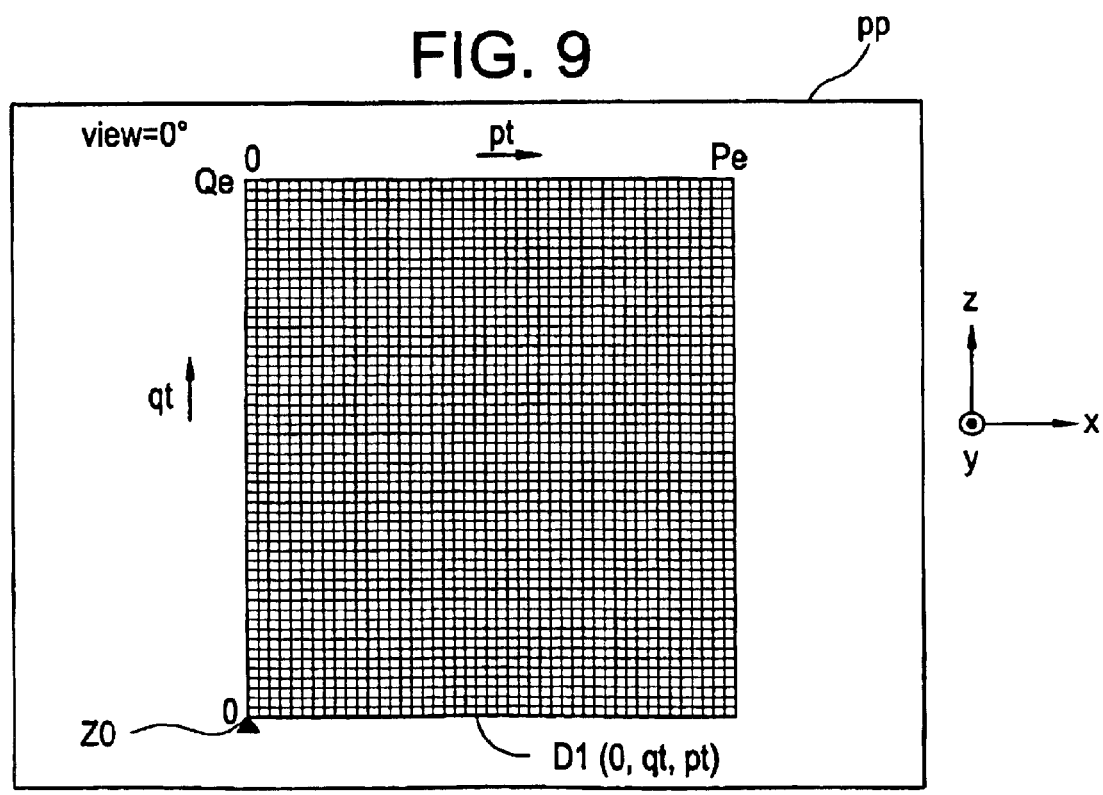

FIG. 15A
FIG. 15B
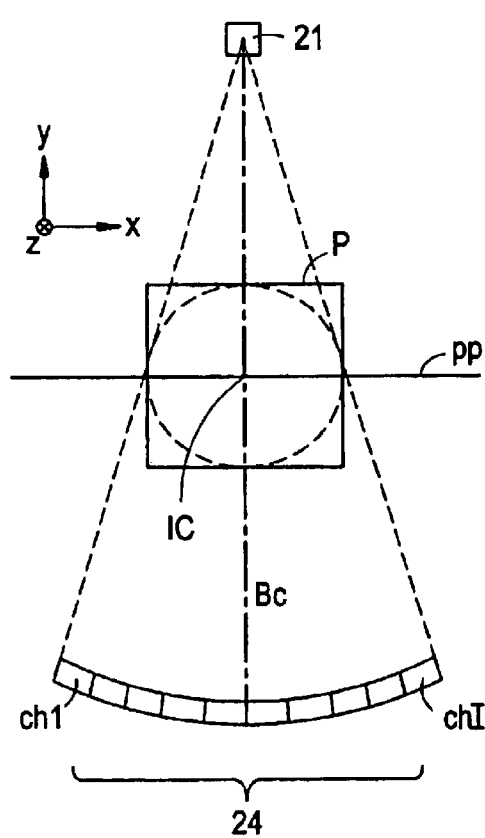
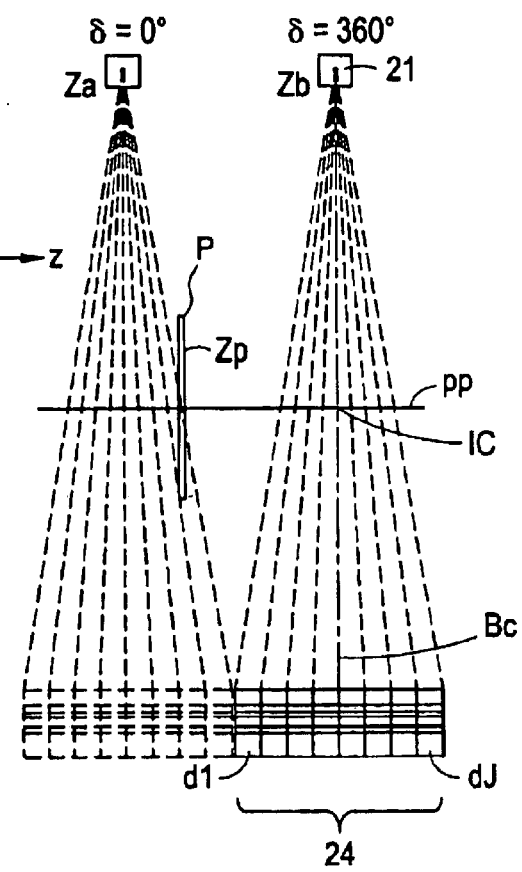

Opposing view to view = 0°

Opposing view to 30°

FIG. 19
32

| y | R(y)_a | str_x | str_qt | Δqt | Δpt | n(y) |
|---|--------|-------|--------|-----|-----|------|
| 0 | | | | | | |
| 1 | | | | | | |
| 2 | | | | | | |
| | | | | | | |
| Ye | | | | | | | view= -45°
view=
view=0°
view=
view=45° -Δview

THREE DIMENSIONAL BACK PROJECTION METHOD AND AN X-RAY CT APPARATUS

BACKGROUND OF THE INVENTION

The present invention relates to a three dimensional back projection method and an X-ray computed tomography (CT) apparatus. More specifically, the present invention relates to a three dimensional back projection method and an X-ray CT apparatus, in the image reconstruction (referred to as cone beam reconstruction) based on the projection data that is gathered by axial scanning or helical scanning by means of a multidetector system, which allow reconstructions to be performed using the projection data precisely corresponding to the X-ray beam passing through the reconstruction area.

To date, the mainstream X-ray CT apparatus typically uses a filtered back projection technique, which reconstructs an image through processes including gathering data, preprocessing, filtering, back projecting and postprocessing.

FIG. 1 schematically shows projection data gathered at a view angle a "view=0°" by scanning with a multidetector 24 and the position of reconstruction area P.

In the back projection methods of the related art, the projection data gathered by the fifth array of detectors that corresponds to the z-coordinate of the reconstruction area P has been used for the projection data at the view angle "view=0°" for use in the image reconstruction.

FIG. 2 is a schematic enlarged view in z-axis of an X-ray beam passing through the reconstruction area P as shown in FIG. 1(b).

Part A of the X-ray beam passing through the reconstruction area P is incident into the fifth array of detectors d5. There may not be any problem in using the projection data collected by the fifth array of detectors d5 as the projection data at a view angle "view=0°" for the reconstruction.

However, part B of the X-ray beam passing through the reconstruction area P is incident into the sixth array of detectors d6, rather than the fifth array of detectors d5. There may arise a problem of discrepancy if the projection data collected by the fifth array of detectors d5 is used is used for the projection data at the view angle "view=0", resulting in a so-called corn angle artifact.

SUMMARY OF THE INVENTION

Therefore, a primary object of the present invention is to provide a three dimensional back projection method and an X-ray CT apparatus, which allow reconstruction to be achieved, in a so-called cone beam reconstruction, by using the projection data in correct correspondence with the X-ray beam passing through the reconstruction area.

In accordance with the first aspect, the present invention, provides a three dimensional back projection method, characterized in that the method comprises: projecting projection data D0 gathered by an axial scan or a helical scan using a multidetector which has a plurality of detector arrays onto a projection plane which is planar to determine planar projection data D1; then projecting the data D1 onto each of pixels consisting a reconstruction area in the direction of X-ray transmission to determine back projection pixel data D2; and adding for each corresponding pixel the back projection pixel data D2 of all views for use in the image reconstruction to determine back projection pixel data D3.

In the three dimensional back projection method in accordance with the above first aspect of the present invention, plane projection data D1 projected from the projection data D0 may be first determined, then the plane projection data D1 will be projected onto the reconstruction area in the direction of X-ray transmission so as to determine back projection pixel data D2. The reconstruction will be thereby allowed to be performed faster by using the projection data correctly corresponding to the X-ray beam passing through the reconstruction area.

It should be noted that the reconstruction area P is in a plane while the multidetector is located in spatial position along a sector of arc. At this point, when directly projecting the data in position at an arcuate sector into the reconstruction area, namely the grid of a coordinate system, coordinate transform will become complex, requiring a certain amount of computation. In addition, the amount of computation will become huge if transforming every pixel in the reconstruction area. In other words, the processing will be complex and time-consuming if determining back projection pixel data D2 directly from projection data D0.

In contrast, the three dimensional back projection method in accordance with the above first aspect of the present invention, instead of directly determining back projection pixel data D2 from projection data D0, plane projection data D1 will be derived from the projection data Projection Data D0, and the plane projection data D1 is used to derive the back projection pixel data D2. At this point, when projecting data located in a plane onto a reconstruction area that is a grid coordinate, a 1st order transform (affine transform) is sufficient to achieve the process by sampling data at a constant sampling pitch. Therefore in view of overall performance, the process will be simplified and become faster.

Preferably, the plane projection data D1 should be interpolated such that the interval between data be sufficiently smaller.

In accordance with the second aspect, the present invention provides a three dimensional back projection method of the configuration as have been described above, characterized in that the method comprises, when defining the direction perpendicular to the rotating plane of X-ray tube or the multidetector or the direction of linear displacement of the helical scan as z-axis, the direction of center axis of the X-ray beam at view=0° as y-axis, and the direction normal to both the z- and y-axis as x-axis, the projection plane being xz plane that passes through the center of rotation in a view angle range which may be delimited as −45°≦view<45° or which primarily includes the same and also includes the periphery thereof, or in a view angle range which may be determined as 135°≦view<225° or which primarily includes the same and also includes the periphery thereof, and the projection plane being yz plane that passes through the center of rotation in a view angle range which may be delimited as 45°≦view<135° or which primarily includes the same and also includes the periphery thereof, or in a view angle range which may be determined as 225°≦view<315° or which primarily includes the same and also includes the periphery thereof.

It should be understood that in this specification different definitions "view=−45°" and "view=315°" are used for the purpose of expression, however those two are equivalent and indicates the same view.

When projecting data onto a projection plane, the precision will become higher if the angle of the line of projecting direction with the projection plane reaches to 90° and become coarser if the angle reaches to 0°.

In the three dimensional back projection method in accordance with the above second aspect of the present invention, the angle of the line of projection direction with the projection plane, i.e., xz plane or yz plane may not become less than approximately 45° the degradation of precision may be suppressed within the tolerance.

In accordance with the third aspect, the present invention provides a three dimensional back projection method of the configuration as have been described above, characterized in that the method comprises determining one set of plane projection data D1 by interpolation/extrapolation delivered from a plurality of sets of projection data D0.

In the three dimensional back projection method in accordance with the above third aspect of the present invention, since one set of plane projection data D1 is derived by the interpolation from a plurality of sets of projection data D0, the density of plane projection data D1 can be sufficiently higher when compared to the pixel density in the reconstruction area. The processing of determining back projection pixel data D2 by projecting plane projection data D1 onto the reconstruction area in the direction of X-ray transmission may be simply a sampling, allowing eliminating interpolation so as to simplify the processing and to accelerate. The interpolation may be used if desired.

In accordance with the fourth aspect, the present invention provides a three dimensional back projection method of the configuration as have been described above, characterized in that the method comprises making a table of addresses and interpolation/extrapolation indices of the plurality of sets of projection data D0 in order to determine one set of plane projection data D1.

Addresses of a plurality of sets of projection data D0 and indices for the interpolation/extrapolation for use in determining one set of plane projection data D1 may be calculated each time one set of plane projection data D1 is to be required, however the calculation time may be a considerable overhead.

In accordance with the above fourth aspect of the present invention, addresses of a plurality of sets of projection data D0 and interpolation/extrapolation indices are preprocessed and are stored in a table to eliminate the overhead as have been described above. In other words, the processing will become faster by making a table.

In accordance with the fifth aspect, the present invention provides a three dimensional back projection method of the configuration as have been described above, characterized in that the method comprises determining a set of plane projection data D1 by interpolation of a plurality of sets of projection data D0; making a table of addresses and interpolation/extrapolation indices for use with a plurality of sets of projection data D0 in order to determine one set of plane projection data D1 in either a view angle range which may be delimited as $-45° \leq view < 45°$ or which primarily includes the same and also includes the periphery thereof, or in a view angle range which may be determined as $135° \leq view < 225°$ or which primarily includes the same and also includes the periphery thereof, or a view angle range which may be delimited as $45° \leq view < 135°$ or which primarily includes the same and also includes the periphery thereof, or in a view angle range which may be determined as $225° \leq view < 315°$ or which primarily includes the same and also includes the periphery thereof, and using the table in other view angle ranges.

When the projection plane is xz plane, which intersects with the revolving center, if geometric relationship of the X-ray tube, detectors, and projection axis in the view angle range of $135° \leq view < 225°$ or range which primarily includes the same and also the periphery thereof is rotated 180° around about the revolving center, the geometric relationship will be matched with that of the X-ray tube, detectors, and projection axis in the view angle range of $-45° \leq view < 45°$ or range which primarily includes the same and also the periphery thereof. Thus addresses of projection data D0 and interpolation/extrapolation indices for determining one set of plane projection data D1 may be shared among both range.

When the projection plane is yz plane, which intersects with the revolving center, if geometric relationship of the X-ray tube, detectors, and projection axis in the view angle range of $45° \leq view < 135°$ or range which primarily includes the same and also the periphery thereof is rotated $-90°$ around about the revolving center, the geometric relationship will be matched with that of the X-ray tube, detectors, and projection axis in the view angle range of $-45° \leq view < 45°$ or range which primarily includes the same and also the periphery thereof, in case in which the projection plane is xz plane, which intersects with the revolving center. Thus, addresses of projection data D0 and interpolation/extrapolation indices for determining one set of plane projection data D1 may be shared among both range.

In addition, when the projection plane is yz plane, which intersects with the revolving center, if geometric relationship of the X-ray tube, detectors, and projection axis in the view angle range of $225° \leq view < 315°$ or range which primarily includes the same and also the periphery thereof is rotated 90° around about the revolving center, the geometric relationship will be matched with that of the X-ray tube, detectors, and projection axis in the view angle range of $-45° \leq view < 45°$ or range which primarily includes the same and also the periphery thereof, in case in which the projection plane is xz plane, which intersects with the revolving center. Thus, addresses of projection data D0 and interpolation/extrapolation indices for determining one set of plane projection data D1 may be shared among both range.

In the three dimensional back projection method in accordance with the above fifth aspect of the present invention, table used either one of the view angle range of $-45° \leq view < 45°$ or range which primarily includes the same and also the periphery thereof, the view angle range of $135° \leq view < 225°$ or range which primarily includes the same and also the periphery thereof, $45° \leq view < 135°$ or range which primarily includes the same and also the periphery thereof, or the view angle range $225° \leq view < 315°$ or range which primarily includes the same and also the periphery thereof may be shared in common with other view angle ranges, allowing the storage required for the table to be minimized.

In accordance with the sixth aspect, the present invention provides a three dimensional back projection method of the configuration as have been described above, characterized in that the method comprises interpolation/extrapolation including the interpolation/extrapolation of 0th order or the interpolation/extrapolation of 1st order.

In the three dimensional back projection method in accordance with the above sixth aspect of the present invention, interpolation/extrapolation of 0th order (i.e., adoption of neighboring data), and interpolation/extrapolation of 1st order (i.e., interpolation/extrapolation may be included using two neighboring data items) so as to facilitate the interpolation/extrapolation.

In accordance with the seventh aspect, the present invention provides a three dimensional back projection method of the configuration as have been described above, characterized in that the method comprises determining one set of back projection pixel data D2 by weighted addition of a plurality of sets of plane projection data D1.

In the three dimensional back projection method in accordance with the above seventh aspect of the present invention, weighted addition of a plurality of sets of data in the same view or in the opposing view in the vicinity of the reconstruction area may be applied.

In accordance with eighth aspect, the present invention provides a three dimensional back projection method of the configuration as above, characterized in that the method comprises the weight of the weighted addition being determined in accordance with the distance from the X-ray focal point to the plane projection data D1.

In general, data D1 of which the distance from the X-ray focal point to the plane projected data D1 is shorter may be considered to include more correctly information about each pixel, in comparison with the data D1 having a larger distance.

Consequently, the three dimensional back projection method in accordance with the above eighth aspect of the present invention may allow determining back projection pixel data D2 in a much more precise fashion.

In accordance with the ninth aspect, the present invention provides a three dimensional back projection method of the configuration as have been described above, characterized in that the method comprises the weight of the weighted addition being determined in accordance with the distance from the X-ray focal point to each pixel in the reconstruction area.

Since the distance from the X-ray focal point to the detectors is constant, data D1 of the case in which the distance from each pixel in the reconstruction area to the X-ray focal point is larger may be considered to include more correctly information about each pixel because in comparison with the data D1 of the case in which the distance to the X-ray focal point is shorter the distance to the detectors is shorter.

Therefore the three dimensional back projection method in accordance with the above ninth aspect of the present invention may allow determining back projection pixel data D2 in a much more precise fashion.

In accordance with the tenth aspect, the present invention provides a three dimensional back projection method of the configuration as have been described above, characterized in that the method comprises the weight of the weighted addition being in common in pixels consisting the reconstruction area which lie on a straight line parallel to the projection plane.

The weight used in the weighted addition may be defined as the ratio of the distance from the X-ray focal point to the plane projection data D1, to the distance from the X-ray focal point to each pixel in the reconstruction area. In this scenario, those pixels which belong to the reconstruction area and reside on the straight line parallel to the projection plane may have the same value of the ratio.

Thus the three dimensional back projection method in accordance with the above tenth aspect of the present invention may allow simplifying the process by sharing the weight in common.

In accordance with the eleventh aspect, the present invention provides a three dimensional back projection method of the configuration as have been described above, characterized in that the method comprises sampling the plane projection data D1 with the starting addresses, sampling pitch, and the number of samples being predefined, in order to select the plane projection data D1 for the weighted addition of the pixels consisting the reconstruction area which reside on a straight line parallel to the projection plane.

For those pixels which belong to the reconstruction area and reside on the straight line parallel to the projection plane, plane projected data D1 used for determining the back projection pixel data D2 may be present on the straight line on the projection plane. By defining the starting address, sampling pitch, and the number of samples, selection will be simple.

Thus the three dimensional back projection method in accordance with the above eleventh aspect of the present invention, plane projection data D1 for determining back projection pixel data D2 may be selected with a simple operation.

In accordance with the twelfth aspect, the present invention provides a three dimensional back projection method of the configuration as have been described above, characterized in that the method comprises making a table of the predefined weight of the weighted addition, starting addresses, sampling pitch and the number of samples.

In the three dimensional back projection method in accordance with the above twelfth aspect of the present invention the operation may be accelerated by making a table.

In accordance with the thirteenth aspect, the present invention provides a three dimensional back projection method of the configuration as have been described above, characterized in that the method comprises putting into the back projection pixel data D2 of a view the result of adding the back projection pixel data D2 of a view and the back projection pixel data D2 of an opposing view with both sets of data multiplied by weighted indices ω a, ω b (where ω a+ω b=1) in correspondence with the angle between the straight line from each pixel of reconstructed area in both views to the X-ray focal point and the reconstructed area.

In general, it may be considered that data may contain more correct information about each pixel if the angle between the straight line connecting each pixel in the reconstruction area to the X-ray focal point and the reconstruction area is closer to 90°.

Thus the three dimensional back projection method in accordance with the above thirteenth aspect of the present invention may allow determining more correctly the back projection pixel data D2.

In accordance with the fourteenth aspect, the present invention provides an X-ray CT apparatus, which comprises: an X-ray tube; a multidetector having a plurality of detector arrays; a scanning means for collecting projection data D0 either while revolving at least one of the X-ray tube and the multidetector around a subject to be imaged or while revolving and moving straight both the X-ray tube and multidetector relative to the subject to be imaged; a plane projection data calculating means for projecting the projection data D0 onto a projection plane which is planar to determine plane projection data D1; a back projection pixel data calculating means for projecting the data D1 onto each of pixels consisting a reconstruction area in the direction of X-ray transmission to determine back projection pixel data D2; a back projection pixel data calculating means for adding for each corresponding pixel the back projection pixel data D2 of all views for use in the image reconstruction to determine back projection pixel data D3.

The X-ray CT apparatus in accordance with the above fourteenth aspect of the present invention may suitably implement the three dimensional back projection method in accordance with the above first aspect of the present invention.

In accordance with the fifteenth aspect, the present invention provides an X-ray CT apparatus of the configuration as have been described above, in which the planar projection data calculator means uses, when defining the direction perpendicular to the rotating plane of X-ray tube or the multidetector or the direction of linear displacement of the helical scan as z-axis, the direction of center axis of the X-ray beam at view=0° as y-axis, and the direction normal to both the z- and y-axis as x-axis, as the projection plane an xz plane that passes through the center of rotation in a view angle range which may be delimited as −45°≦view<45° or which primarily includes the same and also includes the periphery thereof, or in a view angle range which may be determined as 135°≦view<225° or which primarily includes the same and also includes the periphery thereof; and as the projection plane a yz plane that passes through the center of rotation in a view angle range which may be delimited as 45°≦view<135° or which primarily includes the same and also includes the periphery thereof, or in a view angle range which may be determined as 225°≦view<315° or which primarily includes the same and also includes the periphery thereof.

The X-ray CT apparatus in accordance with the above fifteenth aspect of the present invention may suitably implement the three dimensional back projection method in accordance with the above second aspect of the present invention.

In accordance with the sixteenth aspect, the present invention provides an X-ray CT apparatus of the configuration as have been described above, in which the planar projection data calculator means applies interpolation/extrapolation to a plurality of sets of projection data D0 to determine one set of plane projection data D1.

The X-ray CT apparatus in accordance with the above sixteenth aspect of the present invention may suitably implement the above third aspect of the present invention.

In accordance with the seventeenth aspect, the present invention provides an X-ray CT apparatus of the configuration as have been described above, in which the planar projection data calculator means makes use of a table having addresses and interpolation/extrapolation indices of a plurality of sets of projection data D0 set for determining one set of plane projection data D1.

The X-ray CT apparatus in accordance with the above seventeenth aspect of the present invention may suitably implement the three dimensional back projection method in accordance with the above fourth aspect of the present invention.

In accordance with the eighteenth aspect, the present invention provides an X-ray CT apparatus of the configuration as have been described above, in which the planar projection data calculator means determines a set of plane projection data D1 by interpolation of a plurality of sets of projection data D0; and makes a table of addresses and interpolation/extrapolation indices for use with a plurality of sets of projection data D0 in order to determine one set of plane projection data D1 in either a view angle range which may be delimited as −45°≦view<45° or which primarily includes the same and also includes the periphery thereof, or in a view angle range which may be determined as 135°≦view<225° or which primarily includes the same and also includes the periphery thereof, or a view angle range which may be delimited as 45°≦view<135° or which primarily includes the same and also includes the periphery thereof, or in a view angle range which may be determined as 225°≦view<315° or which primarily includes the same and also includes the periphery thereof, and also uses the table in other view angle ranges.

The X-ray CT apparatus in accordance with the above eighteenth aspect of the present invention may suitably implement the three dimensional back projection method in accordance with the above fifth aspect of the present invention.

In accordance with the nineteenth aspect, the present invention provides an X-ray CT apparatus of the configuration as have been described above, in which the interpolation/extrapolation includes the interpolation/extrapolation of 0th order or the interpolation/extrapolation of 1st order.

The X-ray CT apparatus in accordance with the above nineteenth aspect of the present invention may suitably implement the three dimensional back projection method in accordance with the above sixth aspect of the present invention.

In accordance with the twentieth aspect, the present invention provides an X-ray CT apparatus of the configuration as have been described above, in which one set of back projection pixel data D2 is determined by weighted addition of a plurality of sets of plane projection data D1.

The X-ray CT apparatus in accordance with the above twentieth aspect of the present invention may suitably implement the three dimensional back projection method in accordance with the above seventh aspect of the present invention.

In accordance with the twenty first aspect, the present invention provides an X-ray CT apparatus of the configuration as have been described above, in which the weight of the weighted addition is determined in accordance with the distance from the X-ray focal point to the plane projection data D1.

The X-ray CT apparatus in accordance with the above twenty first aspect of the present invention may suitably implement the three dimensional back projection method in accordance with the above eighth aspect of the present invention.

In accordance with the twenty second aspect, the present invention provides an X-ray CT apparatus of the configuration as have been described above, in which the weight of the weighted addition is determined in accordance with the distance from the X-ray focal point to each pixel in the reconstruction area.

The X-ray CT apparatus in accordance with the above twenty second aspect of the present invention may suitably implement the three dimensional back projection method in accordance with the above ninth aspect of the present invention.

In accordance with the twenty third aspect, the present invention provides an X-ray CT apparatus of the configuration as have been described above, in which the weight of the weighted addition is in common in pixels consisting the reconstruction area which lie on a straight line parallel to the projection plane.

The X-ray CT apparatus in accordance with the above twenty third aspect of the present invention may suitably implement the three dimensional back projection method in accordance with the above tenth aspect of the present invention.

In accordance with the twenty fourth aspect, the present invention provides an X-ray CT apparatus of the configuration as have been described above, in which the plane projection data D1 is sampled with the predefined starting addresses, sampling pitch, and the number of samples, in order to select the plane projection data D1 for the weighted addition of the pixels consisting the reconstruction area which lie on a straight line parallel to the projection plane.

The X-ray CT apparatus in accordance with the above twenty fourth aspect of the present invention may suitably implement the three dimensional back projection method in accordance with the above eleventh aspect of the present invention.

In accordance with the twenty fifth aspect, the present invention provides an X-ray CT apparatus of the configuration as have been described above, in which a table having the weight of the weighted addition, starting addresses, sampling pitch and the number of samples predetermined is made in advance.

The X-ray CT apparatus in accordance with the above twenty fifth aspect of the present invention may suitably implement the three dimensional back projection method in accordance with the above twelfth aspect of the present invention.

In accordance with the twenty sixth aspect, the present invention provides an X-ray CT apparatus of the configuration as have been described above, in which back projection pixel data D2 of a view is derived from the result of adding the back projection pixel data D2 of a view and the back projection pixel data D2 of an opposing view after having both sets of data multiplied by respective weighted indice ω a, ω b (where ω a+ω b=1) in correspondence with the angle between the straight line from each pixel of reconstructed area in both views to the X-ray focal point and the reconstructed area.

The X-ray CT apparatus in accordance with the above twenty sixth aspect of the present invention may suitably implement the three dimensional back projection method in accordance with the above thirteenth aspect of the present invention.

In accordance with the three dimensional back projection method and X-ray CT apparatus of the present invention, determined from projection data D0 may be plane projection data D1, which plane projection data D1 may be projected to a reconstruction area in the direction of X-ray transmission to determine back projection pixel data D2, instead of directly determining back projection pixel data D2 from projection data D0, so that reconstruction is allowed by using projection data correctly corresponding to the X-ray beam having passed through the reconstruction area. In addition, the operation will become totally simplified and faster.

Further objects and advantages of the present invention will be apparent from the following description of the preferred embodiments of the invention as illustrated in the accompanying drawings.

BRIEF DESCRIPTION OF THE DRAWINGS

FIG. 1 is a schematic diagram of spatial position of projection data in reconstruction area;

FIG. 4 is a schematic flow diagram of the operation of an X-ray CT apparatus;

FIG. 5 is a schematic flow diagram of the three dimensional back projection method in accordance with the present invention;

FIG. 8 is a schematic diagram indicating plane projected original data at view=0°;

FIG. 9 is a schematic diagram indicating plane projected data at view=0°;

FIG. 13 is an example of lookup table for plane projected data calculation;

FIG. 15 is a schematic diagram indicating an exemplary spatial position of the reconstruction area;

FIG. 19 is an example of lookup table for back plane projection;

DETAILED DESCRIPTION OF THE INVENTION

The present invention will be described in greater details with reference to some preferred embodiments depicted in the accompanying drawings.

Figure 2:
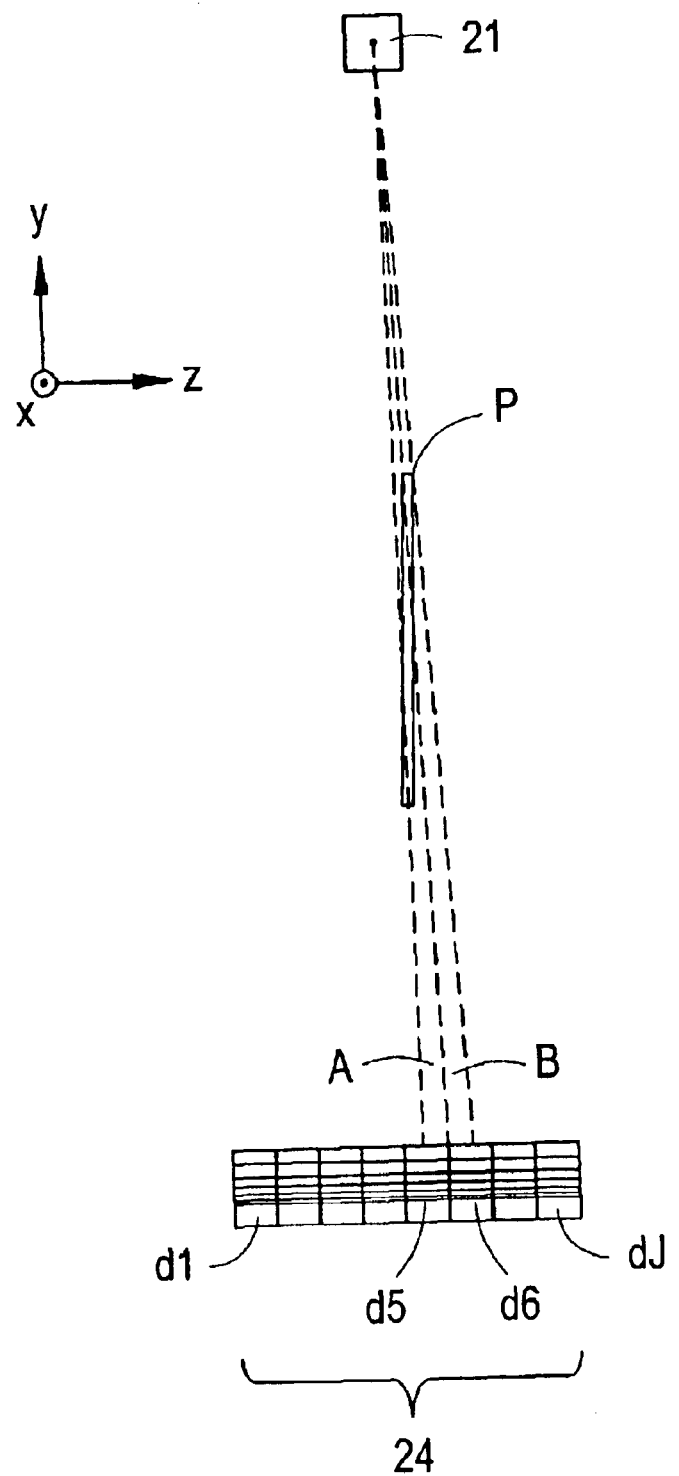
FIG. 2 is a schematic diagram illustrating problems in accordance with the related art.
Figure 3:
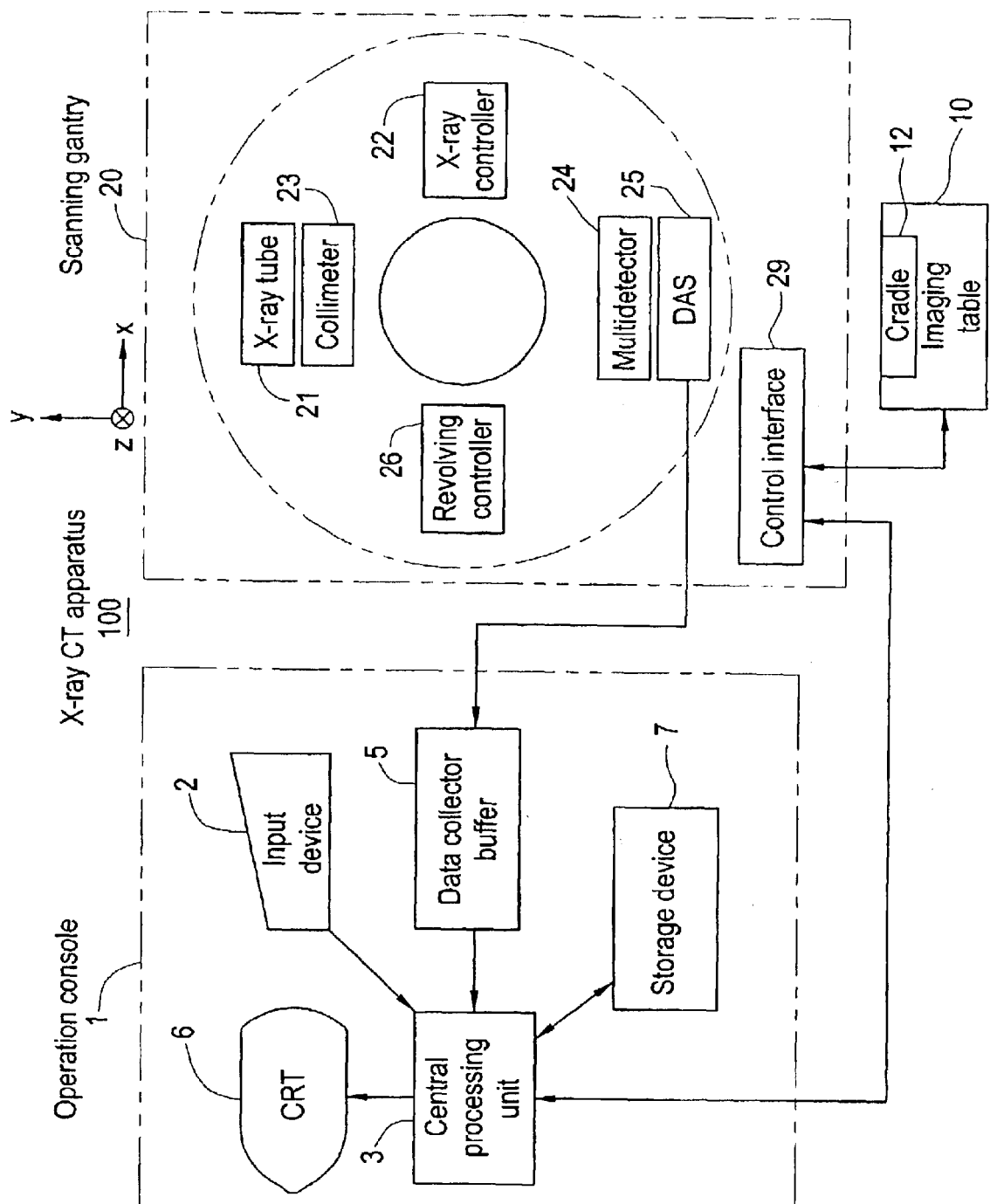
FIG. 3 is a schematic block diagram of an X-ray CT apparatus in accordance with a preferred embodiment of the present invention.

Now referring to FIG. 3, there is shown a schematic block diagram of an X-ray CT apparatus in accordance with one preferred embodiment of the present invention.

The X-ray CT apparatus 100 may include an operation console 1, an imaging table 10, and a scanning gauntry 20.

The operation console 1 may include an input device 2 for accepting input from the operator, a central processing unit 3 for executing three dimensional back projection in accordance with the present invention, a data collector buffer 5 for collecting the projection data obtained by the scanning gauntry 20, a CRT 6 for displaying a CT image reconstructed from the projection data, and a storage device 7 for storing programs, data, and X-ray CT images.

The imaging table 10 may include a cradle 12, which serves for carrying a subject to be imaged thereon to carry in and out to and from the bore (center void) of the scanning gauntry 20. The cradle 12 will be driven by a motor equipped in the imaging table 10.

The scanning gauntry 20 may include an X-ray tube 21, an X-ray controller 22, a collimator 23, a multidetector 24, a data acquisition system (DAS) 25, a revolving controller 26 for revolving the X-ray tube 21 and others around the body axis of the subject, a control interface 29 for sending and receiving control signals and the like to and from the operation console 1 and imaging table 10.

In the following description, it is assumed that a helical scan system is used. Although the axial scan system need not linear translation of the cradle 12, the present invention may also be applied thereto equally as similar to the helical scan system.

Now referring to FIG. 4, there is shown a flow diagram indicating the flow of the operation of X-ray CT apparatus 100.

In step S1, the X-ray tube 21 and the multidetector 24 are revolved around the subject to be imaged by means of the scanning gauntry 20, while moving linearly the cradle 12 to gather projection data D0 (view, δ, j, i), which data is represented by the view angle "view", relative angular difference δ, the number of detector array j, and channel number i. The relative angular difference δ means a parameter indicating how many turn the X-ray tube 21 and the multidetector 24 has been elapsed in the same view, for example, for the first turn δ=360°.

In step S2, the projection data D0 (view, δ, j, i) will be preprocessed (including such operations as offset compensation, logarithm transform, X-ray radiation compensation, and sensitivity compensation).

In step S3, the preprocessed projection data D0 (view, δ, j, i) will be filtered. More specifically, the data will be Fourier transformed, filtered (performed with a reconstruction function), and invert Fourier transformed.

In step S4, the filtered projection data D0 (view, δ, j, i) will be processed by the three dimensional back projection in accordance with the present invention to determine back projection data D3 (x, y). The three dimensional back projection process will be described in greater details below with reference to FIG. 5.

In step S5, back projection data D3 (x, y) will be postprocessed to obtain a CT image.

Now referring to FIG. 5, there is shown a detailed flow diagram of the three dimensional back projection process (step S4)

In step R1, plane projection data D1 (view, qt, pt) that was plane projected to the projection plane will be obtained from the projection data D0 (view, δ, j, i). This operation will be described in greater details below with reference to FIGS. 6 to 14.

In step R2, back projection pixel data D2 (view, x, y) will be obtained from the plane projection data D1 (view, qt, pt) that was plane projected to the projection plane. This operation will be described in greater details below with reference to FIGS. 15 to 19.

In step R3, either a view for 360° worth or a view of "180° worth with fan angle" will be added to the back projection pixel data D2 (view, x, y) in correspondence with pixels to obtain back projection data D3 (x, y). This operation will be described in greater details below with reference to FIG. 20.

Figure 6A:
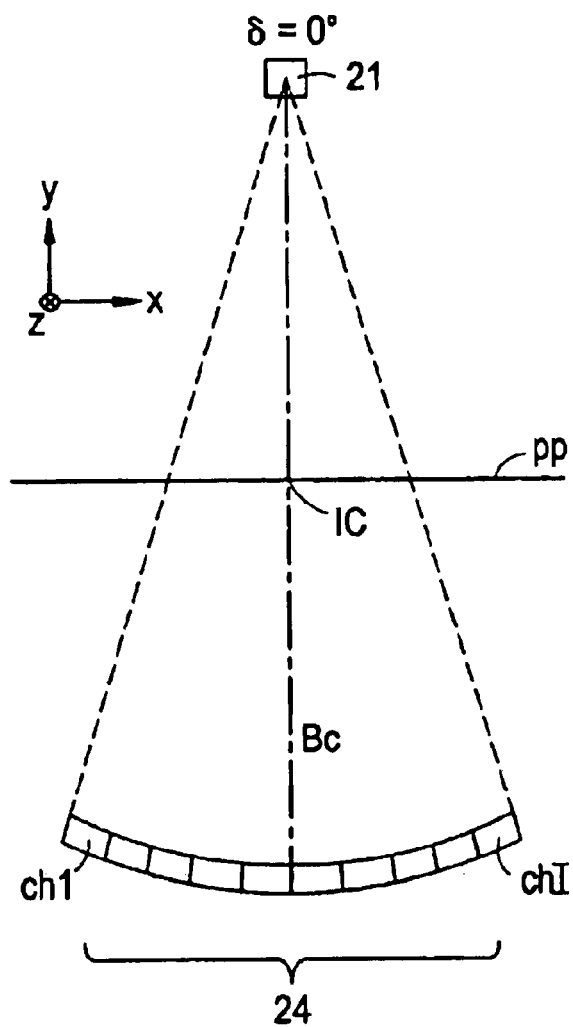
FIG. 6 is a schematic diagram indicating exemplary arrangements of X-ray tube and multidetector at view=0° and δ=0° as well as plane projected original data.
Figure 6B:
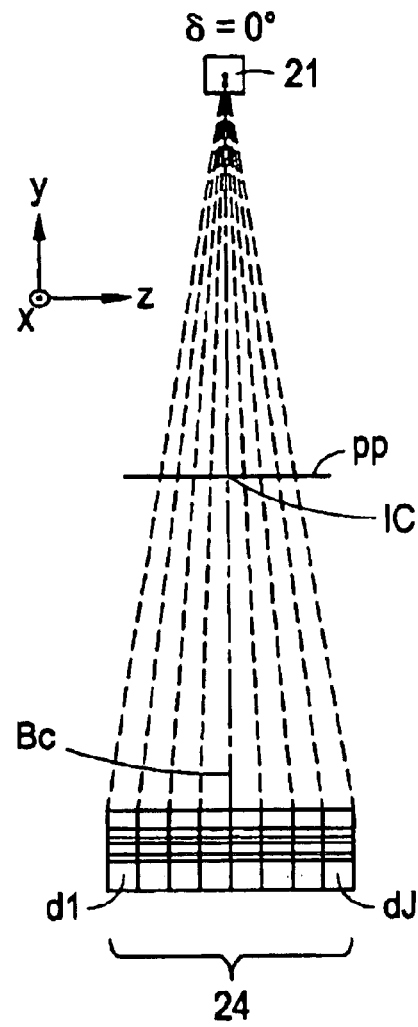
Figure 6C:
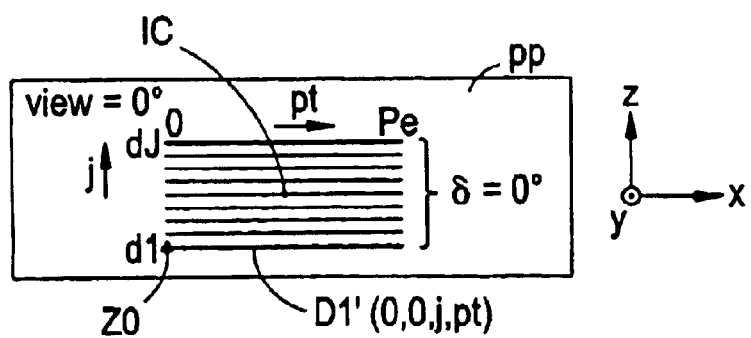

In FIGS. 6(a) and (b) there are shown the arrangement examples of the X-ray tube 21 and the multidetector 24 at view=0°, δ=0° The projection plane pp at this time will be xz plane that passes through the revolving center IC. At the position in the projection plane pp to which each of channels of the multidetector 24 is plane projected in the direction of X-ray transmission, projection data D0 (view=0, δ=0, j, i) obtained from that channel will be multiplied with the distance index and allocated thereto, then interpolated in the direction of the channel to increase sufficiently the data density so that the plane projection data D1' (view=0, δ=0, j, pt) will be obtained as shown in FIG. 6(c). This will be referred to as "plane projecting projection data D0 (view, δ, j, i) to the projection plane pp in the direction of X-ray transmission" hereinbelow.

Here the distance index may be defined as $(r1/r0)^2$ where the distance from the X-ray focal point of the X-ray tube 21 to the channel of the multidetector 24 is r0, the distance from the X-ray tube 21 to the projection position on the projection plane pp is r1.

Z0 in FIG. 6(c) is the origin of coordinate indicating the spatial location of the plane projection data D1' (view=0, δ=0, j=1, pt=0).

Figure 7A:
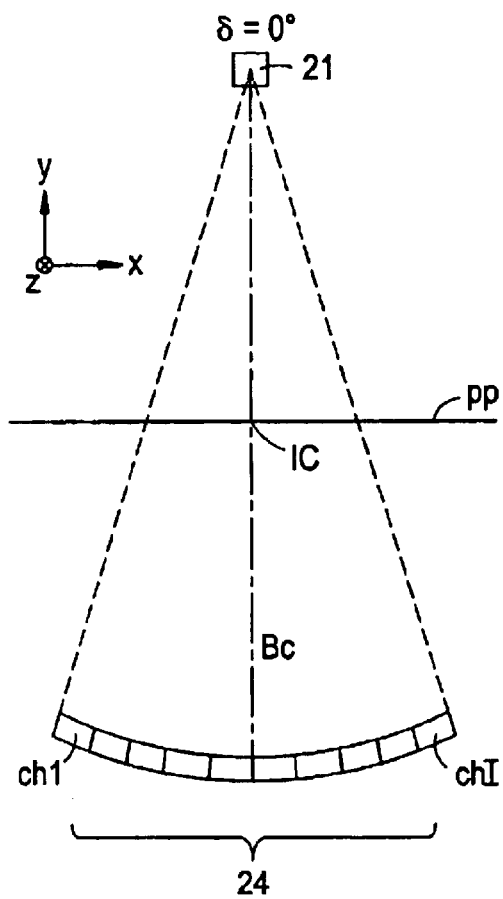
FIG. 7 is a schematic diagram indicating exemplary arrangements of X-ray tube and multidetector at view=0° and δ=360° as well as plane projected original data.
Figure 7B:
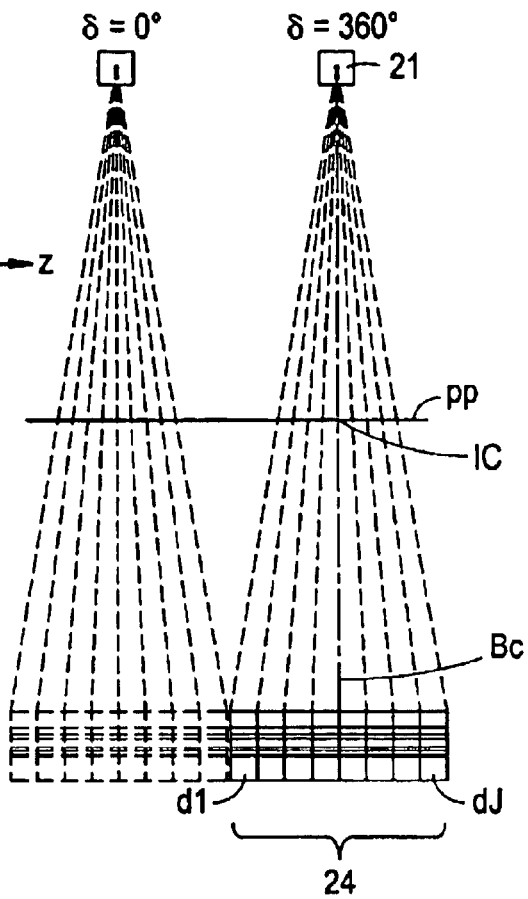
Figure 7C:
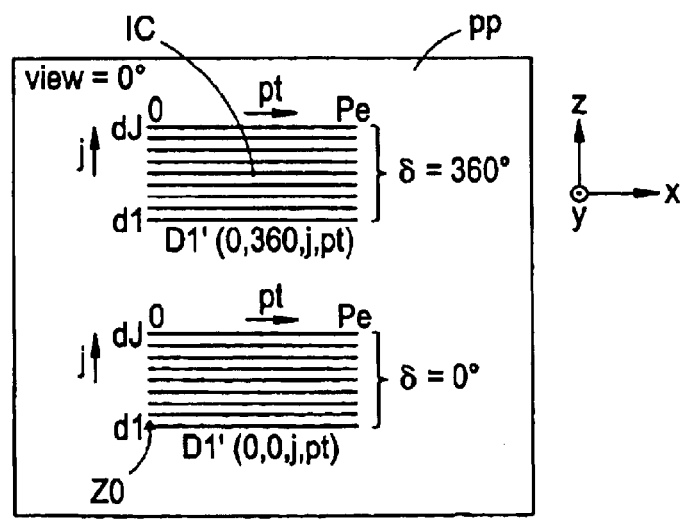

In FIGS. 7(a) and (b) there are shown the arrangement examples of the X-ray tube 21 and the multidetector 24 at view=,0°, δ=360° (i.e., one turn after δ=0°). By plane projecting projection data D0 (view=0, δ=360, j, i) obtained at this situation to the projection plane pp, plane projection data D1' (view=0, δ=360, j, pt) will be obtained, as shown in FIG. 7(c).

In a similar way, as shown in FIG. 8, plane projection data D1' (view=0, δ=720, j, pt) will also be obtained corresponding to view=0°, δ=720° (second turn).

Then, interpolation/extrapolation will be performed on the plane projection data D1' (0, 0, j, i), D1' (0, 360, j, i), D1' (0, 720, j, i) shown in FIG. 8, and plane projection data D1 (view=0, qt, pt) having sufficient density in the direction qt (direction perpendicular to the intersecting line of the reconstruction area P with the projection plane pp) as well as direction pt (direction parallel to the intersecting line of the reconstruction area P with the projection plane pp) will be calculated, as shown in FIG. 9. The density of plane projection data D1 (view=0, qt, pt) is preferably sufficiently higher than the pixel density in the reconstruction area, so as to be able to eliminate the interpolation when determining back projection pixel data D2 from plane projection data D1.

Figure 10:
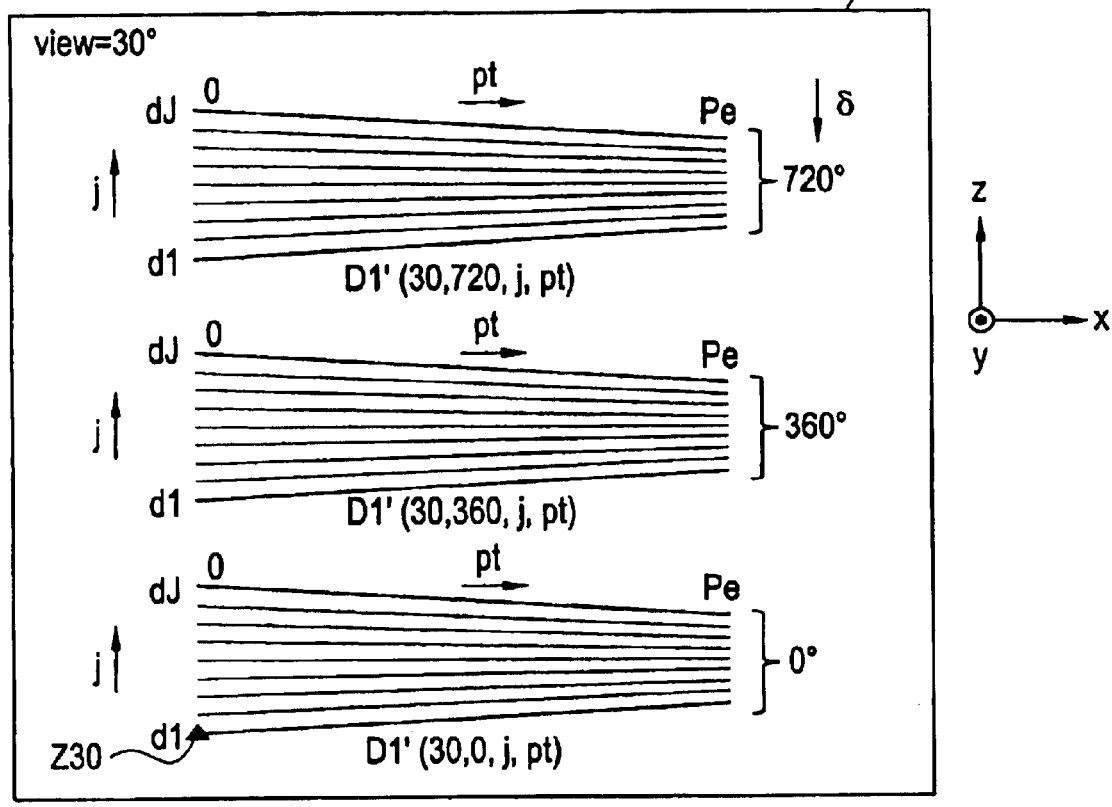
FIG. 10 is a schematic diagram indicating plane projected original data at view=30°.

FIG. 10 shows a schematic diagram of plane projection data D1' (view=30, δ=0, j, pt), D1' (view=30, δ=360, j, pt), D1' (view=30, δ=720, j, pt), corresponding to 0th turn, first turn, second turn at view=30°, respectively.

When compared to view=0°, first channel side of the multidetector 24 reaches to the projection plane pp, and the I-th channel side goes away from the projection plane pp, so that the plane projection data D1' (30, 0, j, pt), D1' (30, 360, j, pt), D1' (30, 720, j, pt), will be wider in the first channel side and narrower in the I-th channel side.

Here Z30 indicates the origin of coordinate indicating the spatial location of the plane projection data D1' (30, 0, 1, 0).

Figure 11:
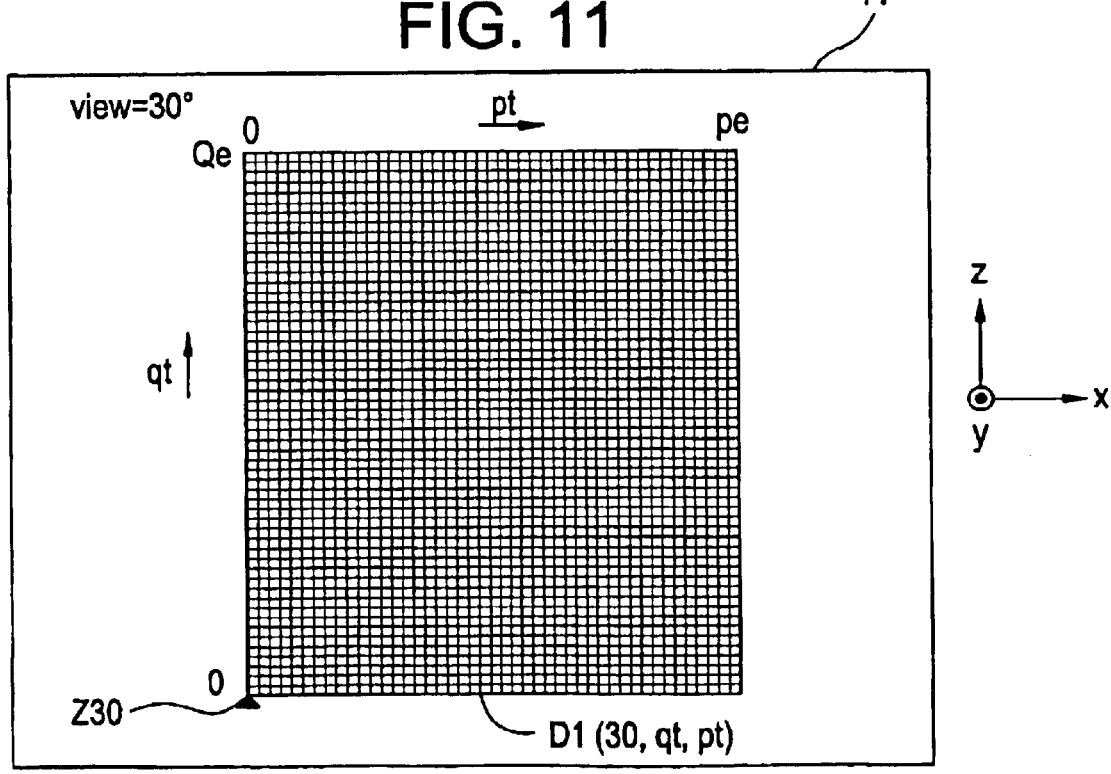
FIG. 11 is a schematic diagram indicating plane projected data at view+30°.

FIG. 11 shows a schematic diagram of plane projection data D1' (30, qt, pt), which is calculated so as to have a sufficient density in both direction qt and direction pt after having performed interpolation/extrapolation on plane projection data D1' (30, 0, j, pt), D1' (30, 360, j, pt), D1' (30, 720, j, pt) as shown in FIG. 10.

Figure 12A:
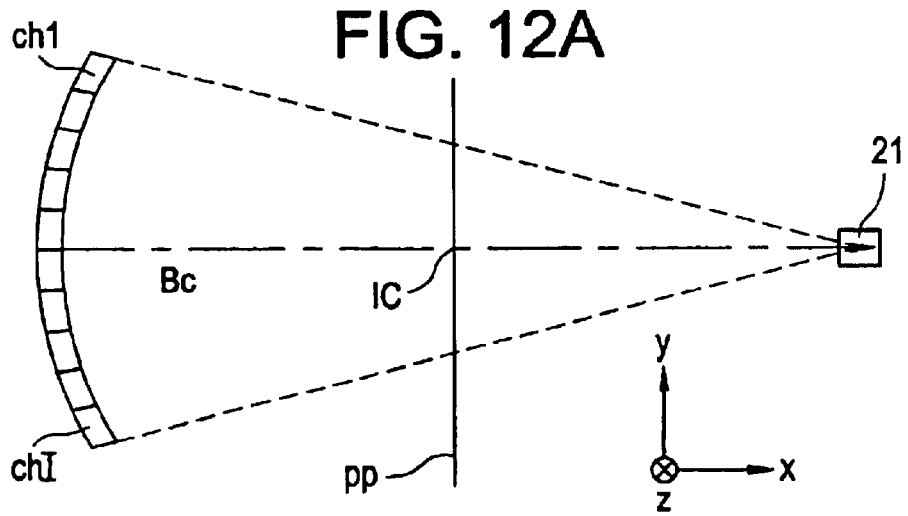
FIG. 12 is a schematic diagram indicating exemplary arrangements of X-ray tube and multidetector at view=90° as well as plane projected original data.
Figure 12B:
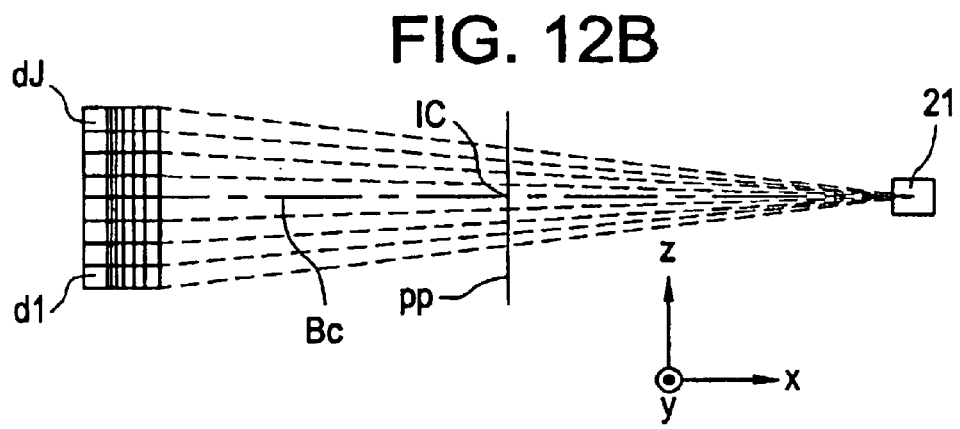
Figure 12C:
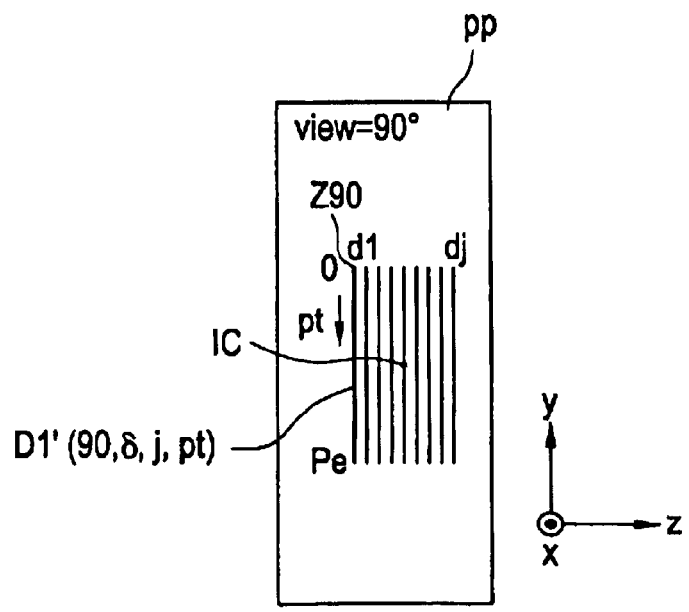

In FIGS. 12(a) and (b) there are shown arrangement examples of the X-ray tube 21 and the multidetector 24 at view=90°. The projection plane pp at this point is yz plane that passes through the revolving center IC. When plane projecting thus obtained projection data D0 (view=90, δ, j, i) onto the projection plane pp, plane projection data D1' (view 90, δ, j, pt) will be obtained, as shown in FIG. 12(c).

As can be seen from the foregoing description, in a view angle range which may be delimited as −45°≦view<45° or which primarily includes the same and also includes the periphery thereof, or in a view angle range which may be determined as 135°≦view<225° or which primarily includes the same and also includes the periphery thereof, xz plane that passes through the revolving center IC will be used for the projection plane pp, in a view angle range which may be delimited as 45°≦view<135° or which primarily includes the same and also includes the periphery thereof, or in a view angle range which may be determined as 225°≦view<315° or which primarily includes the same and also includes the periphery thereof, yz plane that passes through the revolving center IC will be used for the projection plane pp.

In order to determine plane projected data D1 (view, δ, j, pt) from the projection data D0 (view, δ, j, i), it is desirable to have a lookup table 31 for the plane projection stored in the storage device 7 as shown in FIG. 13 to make use of it.

Figures 13A, 13B:
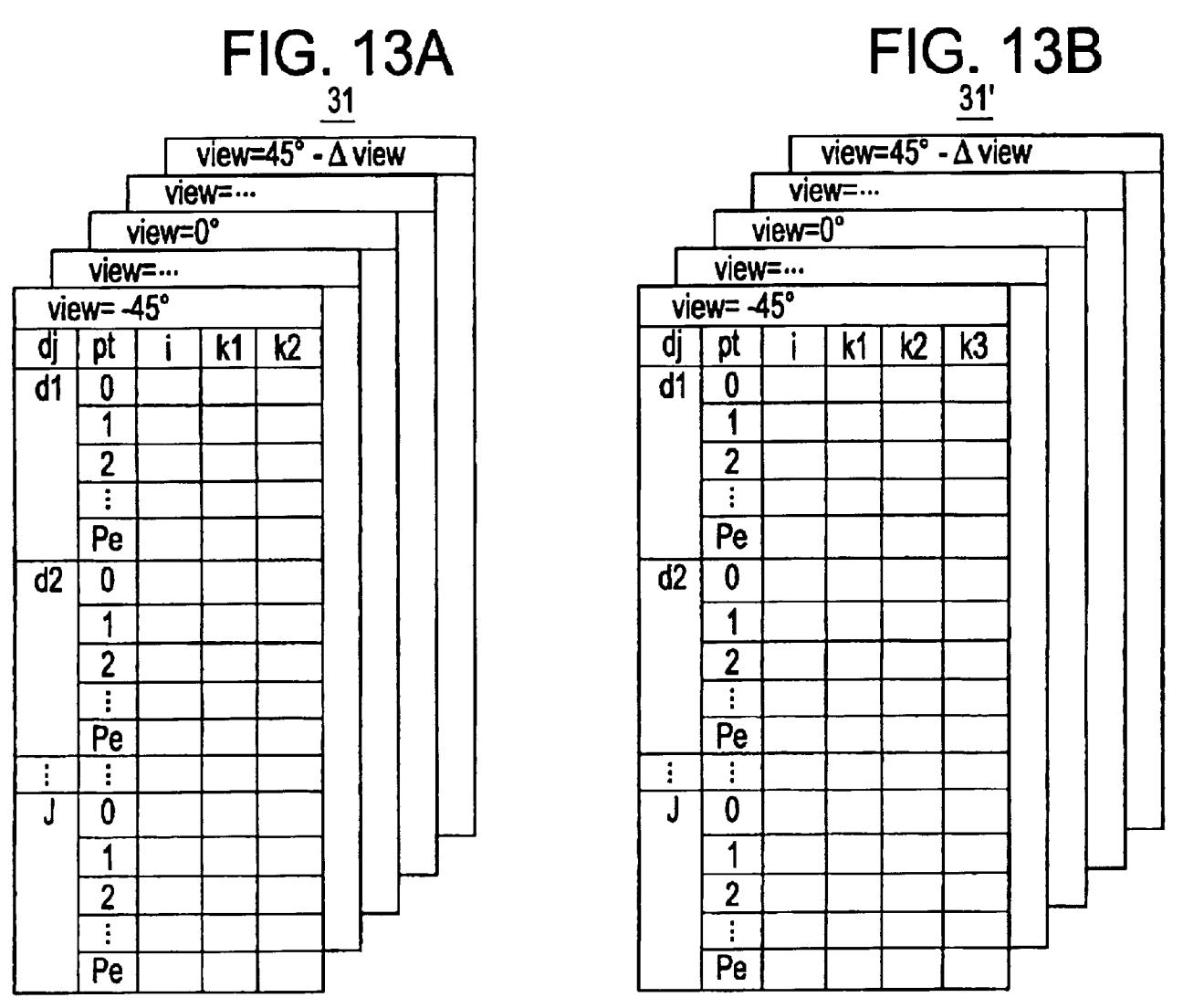

The lookup table 31 as shown in FIG. 13(a) is for determining plane projection data D1' (view, δ, j, pt) by two point interpolation/extrapolation, in which there are precalculated and predefined items including reference channel address i for retrieving projection data D0 at a plurality of channel addresses i, and i+1 for determining plane projection data D1 (view, δ, j, pt) at the coordinate (j, pt) by two point interpolation/extrapolation, and indices k1 and k2 for two point interpolation/extrapolation in the direction pt, for each view angle "view" in a view angle range which may be delimited as −45°≦view<45° (or which primarily includes the same and also includes the periphery thereof).

$$D1(\text{view}, \delta, j, pt) = k1 \times D0(\text{view}, \delta, j, i) + k2 \times D0(\text{view}, \delta, j, i+1)$$

Here, view is a step angle of the view angle (view angle difference between two adjacent views), for example 0.36° for a total of 1000 views.

A lookup table 31' shown in FIG. 13(b) is used for determining plane projection data D1' (view, qt, pt) by three point interpolation/extrapolation, in which there are precalculated and predefined items including reference channel address i for retrieving projection data D0 at a plurality of channel addresses i, i+1, and i+2 for determining plane projection data D1 (view, δ, j, pt) at the coordinate (j, pt) by three point interpolation/extrapolation, and indices k1, k2, and k3 for three point interpolation/extrapolation in the direction pt, for each view angle "view" in a view angle range which may be delimited as −45°≦view<45° (or which primarily includes the same and also includes the periphery thereof).

Figure 14:
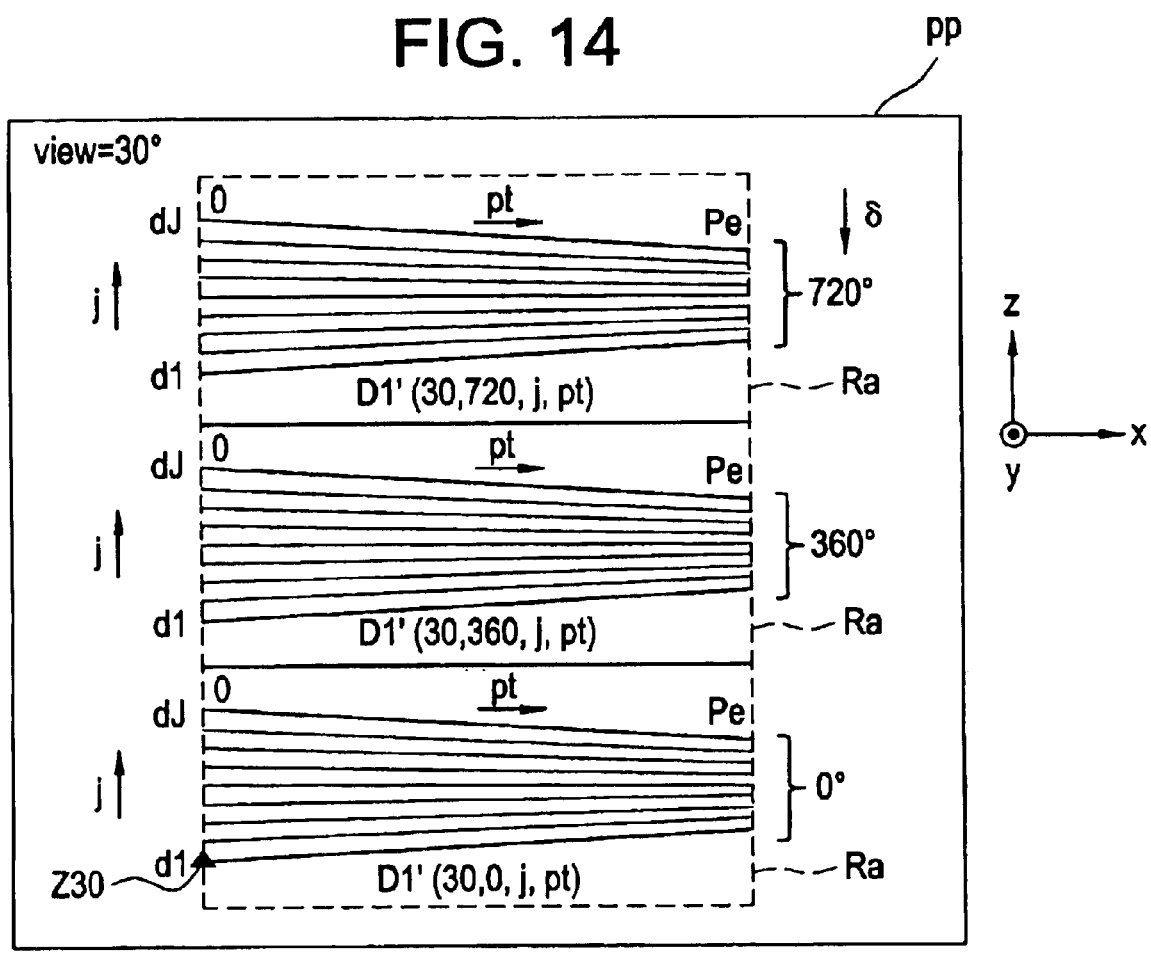
FIG. 14 is a schematic diagram indicating iteration unit of interpolation/extrapolation in the direction qt.

In addition, for the helical scan system, the interpolation indices in the direction qt will be also set in a lookup table as similar to the above lookup table 31, 31' in order to perform interpolation/extrapolation in the direction qt in a similar way. The interpolation in the direction qt will be repeatedly iterated for each oblong area Ra as shown in FIG. 14. Within such an oblong area Ra the operation will be symmetry in the direction qt about the center line.

For the axial scan system, interpolation/extrapolation will be done in only one single oblong area Ra as shown in FIG. 14.

Due to the geometric similarity, the lookup table 31, 31' for use in a view angle range which may be delimited as −45°≦view<45° (or which primarily includes the same and also includes the periphery thereof) may be equally applied to any other view angle ranges than the view angle range which may be delimited as −45°≦view<45° (or which primarily includes the same and also includes the periphery thereof).

Now referring to FIG. 15, there is shown an exemplary spatial position of the reconstruction area P.

There is shown in this figure an exemplary reconstruction area P that resides at the position Zp=Za+(Zb−Za)/4, where Za is the z-axis coordinate of the X-ray tube 21 at view=0° and δ=0° and Zb is the z-axis coordinate of the X-ray tube 21 at view=0°, δ=360°.

Now referring to FIG. 16, there is shown determination of back projection pixel data D2 (0, x, y) by projecting plane projection data D1 (0, qt, pt) to the reconstruction area P in the direction of X-ray transmission.

Figure 16A:
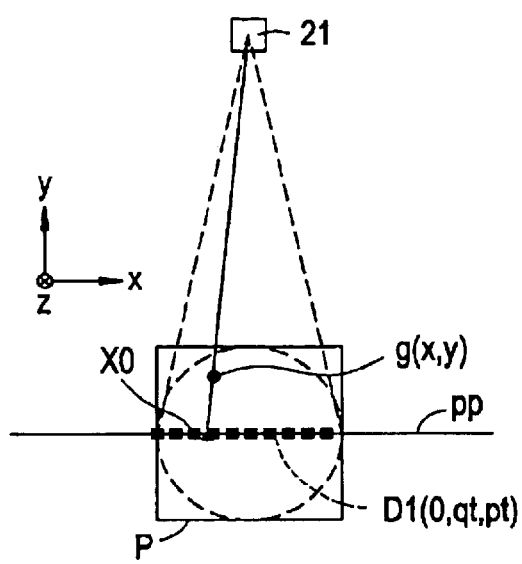
FIG. 16 is determination of back projection pixel data by projecting plane projection data to the reconstruction area in the direction of X-ray transmission at view=0°.

As shown in FIG. 16(a), coordinate X0 may be determined from the intersection of the line connecting the focal point of the X-ray tube 21 at view=0° to pixels g (x, y) on the reconstruction area P with the projection plane pp.

Figure 16B:
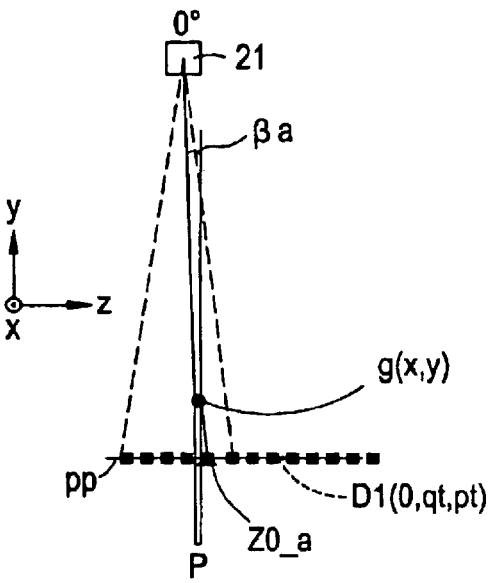

As shown in FIG. 16(b), coordinate Z0_a may be determined from the intersection of the line connecting the focal point of the X-ray tube 21 at view=0° to the pixels g (x, y) on the reconstruction area P with the projection plane pp.

Figure 16C:
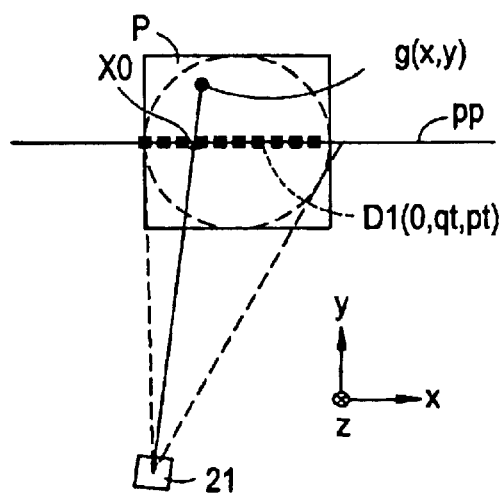
Figure 16D:
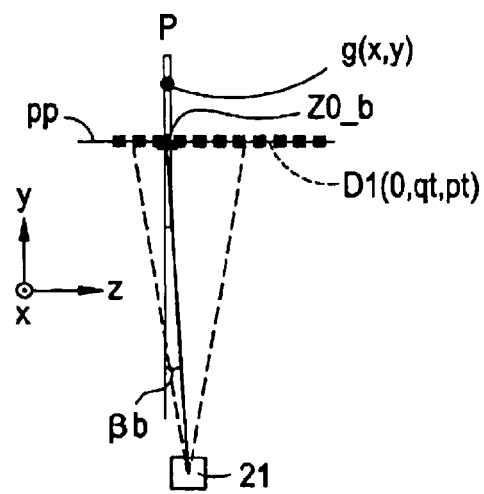

As shown in FIGS. 16(c) and (d), coordinate Z0_b may be determined from the intersection of the line connecting the focal point of the X-ray tube 21 in the opposing view to the pixels g (x, y) on the reconstruction area P with the projection plane pp.

In general, $$\beta b = \beta a + 180° - 2\gamma,$$

where γ is the angle of the line connecting the focal point of the X-ray tube 21 at view=β a to the pixels g (x, y) on the reconstruction area P with respect to the axis Bc of X-ray beam, and its opposing view is view 32 δ b.

Next, plane projection data D1 (0, qt_a, pt) will be determined corresponding to the coordinate (X0, Z0_a). In addition, plane projection data D1 (0, qt_b, pt) will also be determined corresponding to the coordinate (X0, Z0_b).

Then, back projection pixel data D2 (0, x, y) will be delivered from the equation given by $$D2(0, x, y)\_a = (r0\_0a/r0\_1a)^2 D1(0, qt\_a, pt)$$

where r0_0a is the distance from the X-ray focal point of the X-ray tube 21 to the plane projection data D1 (0, qt a, pt) at view=0°, and r0_1a is the distance from the X-ray focal point of the X-ray tube 21 to the pixels g (x, y).

Also, back projection pixel data D2 (0, x, y)_b at view=0° in the opposing view will be given by $$D2(0, x, y)\_b = (r0\_0b/r0\_1b)^2 D1(0, qt\_b, pt)$$

where r0_0b is the distance from the X-ray tube 21 to the plane projection data D1 (0, qt_b, pt) in the opposing view, and r0_1b is the distance from the X-ray tube 21 to the pixels g (x, y).

Then, back projection pixel data D2 (0, x, y) will be given by adding back projection pixel data D2 (0, x, y)_a to D2 (0, x, y)_b after each having multiplied by cone beam reconstruction weight indices depending on the angle α a and α b shown in FIG. 16, ω a and ω b respectively:

$$D2(0, x, y) = \omega a\, D2(0, x, y)\_a + \omega b\, D2(0, x, y)\_b$$

The angle α a is the angle of the X-ray beam passing through the pixels g (x, y) at view=0° with the plane of reconstruction area P. Also, the angle α b is the angle of the X-ray beam passing through the pixels g (x, y) in the opposing view with the plane of reconstruction area P. In addition, ω a+ω b=1. The addition after multiplication with cone beam reconstruction weight indices ω a, ω b allow decreasing cone angle artifact.

For example, values for the cone beam reconstruction weight indices ω a, ω b maybe obtained from the following equation, where max [ ] is a function that selects larger one of values, and ½ of fan-beam angle is γ max:

$$g\ a=\max\ [0,\ \{(\pi/2+\gamma\max)-|\beta a|\}]|\tan\ (\alpha a)|$$

$$g\ b=\max\ [0,\ \{(\pi/2+\gamma\max)-|\beta b|\}]|\tan\ (\alpha b)|$$

$$x\ a=2\times g\ a^q/(g\ a^q+g\ b^q)$$

$$x\ b=2\times g\ a^q/(g\ a^Q+g\ b^q)$$

$$\omega a=xa^2(3-2xa)$$

$$\omega b=xb^2(3-2xb)$$

(for example, q=1)

Now referring to FIG. 17, there is shown determination of back projection pixel data D2 (30, x, y) by projecting plane projection data D1 (30, qt, pt) into the reconstruction area P in the direction of X-ray transmission.

Figure 17A:
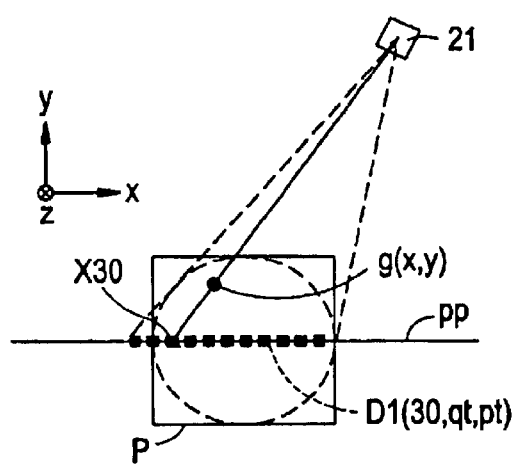
FIG. 17 is determination of back projection pixel data by projecting plane projection data to the reconstruction area in the direction of X-ray transmission at view=30°.

As shown in FIG. 17(a), coordinate X30 may be determined from the intersection of the line connecting the focal point of the X-ray tube 21 at view=30° to the pixels g (x, y) on the reconstruction area P with the projection plane pp.

Figure 17B:
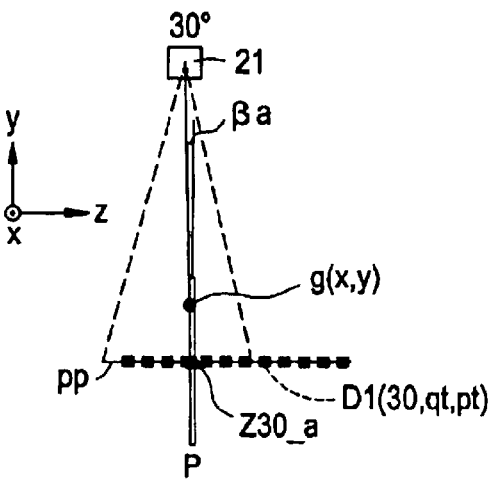

Also as shown in FIG. 17(b), coordinate Z30_a may be determined from the intersection of the line connecting the focal point of the X-ray tube 21 at view=30° and δ=0° to the pixels g (x, y) on the reconstruction area P with the projection plane pp.

Figure 17C:
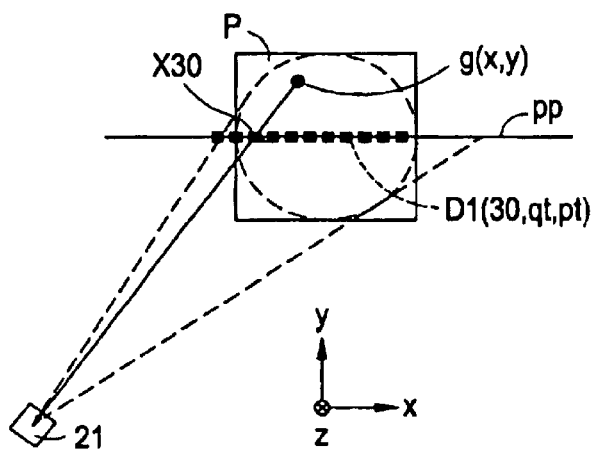
Figure 17D:
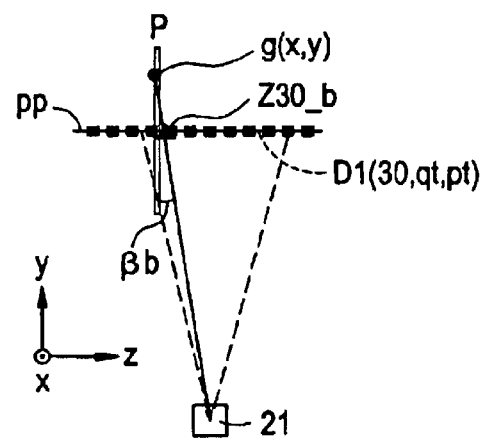

Moreover, as shown in FIGS. 17(c) and (d), coordinate Z30_b may be determined from the intersection of the line connecting the focal point of the X-ray tube 21 in the opposing view to the pixels g (x, y) on the reconstruction area P with the projection plane pp.

Then, back projection pixel data D2 (30, x, y) will be given in a similar way to the foregoing description.

Similarly, back projection pixel data D2 (view, x, y) for any views required for reconstruction will be determined.

Preferably, back projection pixel data D2 (view, x, y)_a and D2 (view, x, y)_b for the pixels g (x, y) present on the line parallel to the projection plane pp will be sequentially determined.

Figure 18:
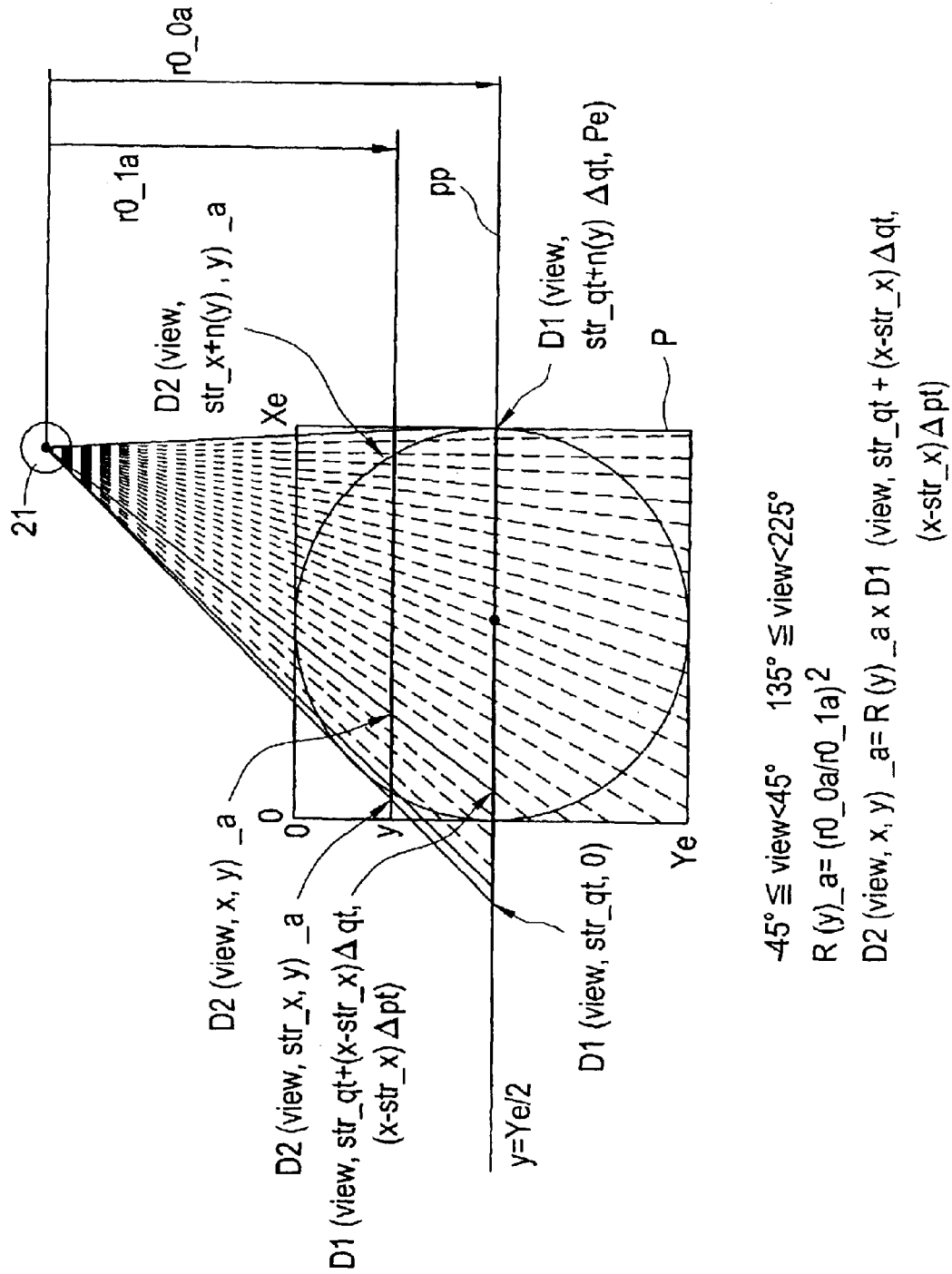
FIG. 18 is consecutive determination of back projection pixel data for pixels lying on a line parallel to the projection plane.

For example, as shown in FIG. 18, when the reconstruction area P is a plane parallel to xy plane, and the projection plane pp is xz plane, back projection pixel data D2 (view, str_x, y)_a to D2 (view, str_x+n(y), y)_a for the pixels g (x, y) present on the line parallel to the x-axis are preferably determined consecutively.

In this case, weight R (y)_a for the pixels g (x, y) present on the line parallel to the x-axis may be $(r0\_1a/r0\_0a)^2$, which is shared in common. Therefore, $$D2(\text{view},\ x,\ y)\_a=R(y)\_a\times D1\ (\text{view},\ str\_qt+(x-str\_x)\ \Delta qt,\ str\_pt+(x-str\_x)\Delta pt),$$

in which by varying from x=str_x to x=str_x+n (y), back projection pixel data D2 (view, str_x, y) to D2 (view, str_x+n (y), y) for pixels g (x, y) present on the line parallel to the x-axis can be consecutively determined.

Now referring to FIG. 19, there is shown a schematic diagram of a lookup table 32 for back projection stored in the storage device 7.

Back projection pixel data D2 may be preferably determined from plane projection data D1 (view, qt, pt) by making use of this lookup table 32 for back projection.

In the lookup table 32, for each view angle "view" in the view angle range which may be delimited as −45°≦view<45° (or which primarily includes the same and als includes the periphery thereof), there are precalculated and predefined y coordinates "y" of back projection pixel data D2 (y coordinates of the line), weights R (y)_a=(r0_0a/r0_1a)² as a parameter of transform for determining one item of back projection pixel data D2 (view, x, y)_a from one item of plane projection data D1 (view, qt, pt), starting addresses str_x str_qt, sampling pitches Δqt, Δpt, the number of samples n (y).

Due to the geometric similarity, the lookup table 32 for use in a view angle range which may be delimited as −45°≦view<45° (or which primarily includes the same and also includes the periphery thereof) may be equally applied to any other view angle ranges than the view angle range which may be delimited as −45°≦view<45° (or which primarily includes the same and also includes the periphery thereof).

Figure 20:
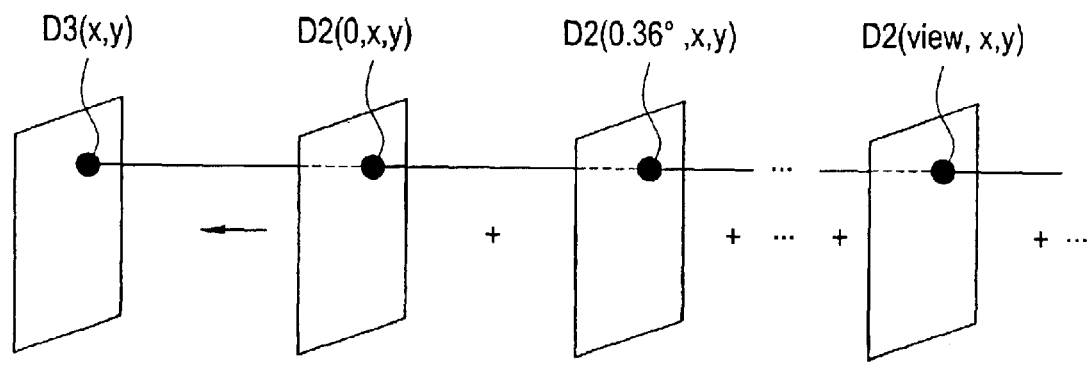
FIG. 20 is determination of back projection pixel data by adding back projection pixel data of all views for each corresponding pixel.

Now referring to FIG. 20, there is shown determination of back projection data D3 (x, y) by adding back projection pixel data D2 (view, x, y) of all views for each corresponding pixel. Namely, D3 (x, y)=viewsΣD2 (view, x, y).

In accordance with the X-ray CT apparatus 100 as have been described above, by determining plane projection data D1 from projection data D0, and determining back projection pixel data D2 therefrom by projecting plane projection data D1 to the reconstruction area in the direction of X-ray transmission, reconstruction will be performed by using projection data correctly corresponding to the X-ray beam passing through the reconstruction area. In addition, the operation will become totally simplified and faster.

In the foregoing description, 1st order interpolation/extrapolation has been envisioned. However, interpolation/extrapolation of 0th order or interpolation/extrapolation of 2nd order or more may be equally applied.

Also in the foregoing description, a helical interpolation using two sets of data D2 originated from mutually opposing views has been envisioned. However a helical interpolation using two sets of data D2 originated from the same view.

In addition, in the foregoing description, the view for the center axis Bc of X-ray beam to be parallel to the y-axis is termed as view=0°. However, any other given angle may be defined as view=0°.

Furthermore, in the foregoing preferred embodiment, an X-ray CT apparatus for medical use has been envisioned. However the present invention may be equally applied to the X-ray CT apparatus for industrial use.

Many widely different embodiments of the invention may be configured without departing from the spirit and the scope of the present invention. It should be understood that the present invention is not limited to the specific embodiments described in the specification, except as defined in the appended claims.

What is claimed is:

1. A three dimensional back projection method comprising the steps of:
 defining a direction perpendicular to at least one of a rotating plane of an X-ray tube, a multidetector, and a direction of linear displacement of a helical scan as a z-axis, a direction of a center axis of an X-ray transmission beam at view=0° as a y-axis, and a direction normal to both the z- and y-axis as an x-axis;
 defining a first xz projection plane as the projection plane that passes through a center of rotation in a view angle range that is approximately −45°≦view<45° and also includes the periphery thereof or in a view angle range that is approximately 135°≦view<225° and also includes the periphery thereof;

projecting projection data D0 gathered by at least one of an axial scan and the helical scan, using the multidetector, onto a projection plane which is planar to determine planar projection data D1, the multidetector comprising a plurality of detector arrays;

defining a second yz projection plane as the projection plane that passes through the center of rotation in a view angle range that is approximately 45°≦view<135° and also includes the periphery thereof or in a view angle range that is approximately 225°≦view<315° and also includes the periphery thereof;

projecting the data D1 onto a reconstruction area in a direction of the X-ray transmission beam to determine back projection pixel data D2, the reconstruction area comprising a plurality of pixels; and adding for each corresponding pixel the back projection pixel data D2 of all views for use in an image reconstruction plane to determine back projection pixel data D3.

2. A three dimensional back projection method according to claim 1, further comprising the step of:
determining one set of plane projection data D1 by interpolation/extrapolation delivered from a plurality of sets of projection data D0.

3. A three dimensional back projection method according to claim 2, further comprising the step of:
making a table of addresses and interpolation/extrapolation indices of said plurality of sets of projection data D0 in order to determine one set of plane projection data D1.

4. A three dimensional back projection method according to claim 1, further comprising the steps of:
determining a set of plane projection data D1 by interpolation of a plurality of sets of projection data D0;
making a table of addresses and interpolation/extrapolation indices for use with a plurality of sets of projection data D0 in order to determine one set of plane projection data D1 in either a view angle range that is approximately −45°≦view<45° and also includes the periphery thereof, or in a view angle range that is approximately 135°≦view<225° and also includes the periphery thereof, or a view angle range that is approximately 45°≦view<135° and also includes the periphery thereof, or in a view angle range that is approximately 225°≦view<315° and also includes the periphery thereof, and using said table in other view angle ranges.

5. A three dimensional back projection method according to claim 1, further comprising the step of:
determining one set of back projection pixel data D2 by weighted addition of a plurality of sets of plane projection data D1.

6. A three dimensional back projection method comprising the steps of:
projecting projection data D0 gathered by at least one of an axial scan and a helical scan, using a multidetector, onto a projection plane which is planar to determine planar projection data D1, the multidetector comprising a plurality of detector arrays;
projecting the data D1 onto a reconstruction area in a direction of an X-ray transmission beam to determine back projection pixel data D2, the reconstruction area comprising a plurality of pixels;
putting into the back projection pixel data D2 of a view the result of adding the back projection pixel data D2 of a view and the back projection pixel data D2 of an opposing view after having both sets of data multiplied by respective weighted indices ωa, ωb (where ωa+ωb=1) in correspondence with an angle between a straight line from each pixel of the reconstruction area in both views to an X-ray focal point and an image; and
adding for each corresponding pixel the back projection pixel data D2 of all views for use in the image reconstruction plane to determine back projection pixel data D3.

7. An X-ray CT apparatus comprising:
an X-ray tube;
a multidetector having a plurality of detector arrays;
a scanning device for collecting projection data D0 either while revolving at least one of said X-ray tube and said multidetector around a subject to be imaged or while revolving and moving straight both said X-ray tube and multidetector relative to said subject to be imaged;
a planar projection data calculating device for projecting said projection data D0 onto a projection plane which is planar to determine plane projection data D1;
a back projection pixel data calculating device for projecting said data D1 onto a reconstruction area in a direction of an X-ray transmission beam to determine back projection pixel data D2, said reconstruction area comprising a plurality of pixels; and
a back projection pixel data calculating device for adding for each corresponding pixel in the back projection pixel data D2 of all views for use in image reconstruction to determine back projection pixel data D3, wherein one set of back projection pixel data D2 is determined by weighted addition of a plurality of sets of plane projection data D1, and wherein the weight of said weighted addition is determined in accordance with an angle made of a straight line lying from each pixel of the reconstruction area in a view to an X-ray focal point with the reconstruction area as well as in accordance with an angle made of a straight line lying from each pixel of the reconstruction area in an opposing view to an X-ray focal point with the reconstruction area.

8. An X-ray CT apparatus according to claim 7, wherein said planar projection data calculating device is further configured to,
define a direction perpendicular to at least one of a rotating plane of the X-ray tube, the multidetector, and a direction of linear displacement of the helical scan as a z-axis, a direction of a center axis of the X-ray beam at view=0° as a y-axis, and a direction normal to both the z- and y-axis as an x-axis,
define a first xz projection plane as the projection plane that passes through a center of rotation in a view angle range that is approximately −45°≦view<45° and also includes the periphery thereof or in a view angle range that is approximately 135°≦view<225° and also includes the periphery thereof; and
define a second yz projection plane as the projection plane that passes through the center of rotation in a view angle range that is approximately 45°≦view<135° and also includes the periphery thereof or in a view angle range that is approximately 225°≦view<315° and also includes the periphery thereof.

9. An X-ray CT apparatus according to claim 8, wherein said planar projection data calculating device determines a set of plane projection data D1 by interpolation of a plurality of sets of projection data D0; and makes a table of addresses and interpolation/extrapolation indices for use with a plurality of sets of projection data D0 in order to determine one set of plane projection data D1 in either a view angle range that is approximately $-45° \leq \text{view} < 45°$ and also includes the periphery thereof, or in a view angle range that is approximately $135° \leq \text{view} < 225°$ and also includes the periphery thereof, or a view angle range that is approximately $45° \leq \text{view} < 135°$ and also includes the periphery thereof, or in a view angle range that is approximately $225° \leq \text{view} < 315°$ and also includes the periphery thereof, and also uses said table in other view angle ranges.

10. An X-ray CT apparatus according to claim 7, wherein said planar projection data calculating device applies interpolation/extrapolation to a plurality of sets of projection data D0 to determine one set of plane projection data D1.

11. An X-ray CT apparatus according to claim 10, wherein said planar projection data calculating device uses a table having addresses and interpolation/extrapolation indices of a plurality of sets of projection data D0 set for determining one set of plane projection data D1.

12. An X-ray CT apparatus according to claim 10, wherein said interpolation/extrapolation includes the interpolation/extrapolation of an nth order.

13. An X-ray CT apparatus according to claim 7, wherein the weight of said weighted addition is determined in accordance with the distance from each pixel in the reconstruction area to the plane projection data D1.

14. An X-ray CT apparatus according to claim 7, wherein the weight of said weighted addition is determined in accordance with the distance from an X-ray focal point to each pixel in the reconstruction area.

15. An X-ray CT apparatus according to claim 7, wherein the weight of said weighted addition is in common in pixels located in the reconstruction area which lies on a straight line parallel to the projection plane.

16. An X-ray CT apparatus according to claim 15, wherein said plane projection data D1 is sampled with predefined starting addresses, sampling pitch, and the number of samples, in order to select said plane projection data D1 for said weighted addition of the pixels in said reconstruction area which lies on a straight line parallel to the projection plane.

17. An X-ray CT apparatus according to claim 16, wherein a table having the weight of said weighted addition, starting addresses, sampling pitch, and the number of samples predetermined is made in advance.

* * * * *

UNITED STATES PATENT AND TRADEMARK OFFICE
CERTIFICATE OF CORRECTION

PATENT NO. : 6,845,144 B2 Page 1 of 1
APPLICATION NO. : 10/360588
DATED : January 18, 2005
INVENTOR(S) : Nishide et al.

It is certified that error appears in the above-identified patent and that said Letters Patent is hereby corrected as shown below:

In Claim 6, column 18, line 6, after "an image" insert -- reconstruction plane --.

Signed and Sealed this

Ninth Day of January, 2007

JON W. DUDAS
*Director of the United States Patent and Trademark Office*